US009220567B2

(12) United States Patent
Sutherland et al.

(10) Patent No.: US 9,220,567 B2
(45) Date of Patent: Dec. 29, 2015

(54) MICROSURGICAL ROBOT SYSTEM

(75) Inventors: Garnette Roy Sutherland, Calgary (CA); Deon Francois Louw, Calgary (CA); Paul Bradley McBeth, Calgary (CA); Tim Fielding, Brampton (CA); Dennis John Gregoris, Toronto (CA)

(73) Assignee: NEUROARM SURGICAL LTD., Alberta (CA)

( * ) Notice: Subject to any disclaimer, the term of this patent is extended or adjusted under 35 U.S.C. 154(b) by 755 days.

(21) Appl. No.: 11/735,983

(22) Filed: Apr. 16, 2007

(65) Prior Publication Data

US 2008/0004632 A1 Jan. 3, 2008

Related U.S. Application Data

(63) Continuation of application No. 11/562,768, filed on Nov. 22, 2006, which is a continuation of application No. 10/639,692, filed on Aug. 13, 2003, now Pat. No. 7,155,316.

(60) Provisional application No. 60/402,724, filed on Aug. 13, 2002.

(51) Int. Cl.
*A61B 19/00* (2006.01)
*A61B 17/00* (2006.01)

(52) U.S. Cl.
CPC .............. *A61B 19/22* (2013.01); *A61B 19/2203* (2013.01); *A61B 19/5212* (2013.01);
(Continued)

(58) Field of Classification Search
CPC ............... A61B 19/22; A61B 19/2203; A61B 2019/5287; A61B 19/5212; A61B 19/5223; A61B 19/5244; A61B 19/54; A61B 19/56; A61B 2017/00911; A61B 2019/2223; A61B 2019/223; A61B 2019/2234; A61B 2019/2242; A61B 2019/2269; A61B 2019/2288; A61B 2019/2292; A61B 2019/2283; A61B 2019/2296; A61B 2019/464; A61B 2019/502; A61B 2019/5236; A61B 2019/5259; B25J 9/1689; B25J 9/1664; B25J 9/1694
USPC ............ 128/897, 923; 340/3.5; 600/101, 102, 600/109, 118, 130, 205, 426, 429, 595; 606/1, 130; 700/247, 248, 249, 256, 700/258, 259, 264; 318/568.11; 901/1, 2, 9
See application file for complete search history.

(56) References Cited

U.S. PATENT DOCUMENTS

| 3,171,549 A | 3/1965 | Orloff | 414/6 |
| 3,241,687 A | 3/1966 | Orloff | 414/5 |

(Continued)

FOREIGN PATENT DOCUMENTS

| CA | 2246369 C | 3/1997 |
| EP | 0886786 B1 | 3/1997 |

(Continued)

OTHER PUBLICATIONS

Tjin et al.; Fiber optic pressure sensor using a fiber Bragg grating; Proc. SPIE 3429; Current Developments in Optical Design and Engineering VII, 123; Oct. 1998; pp. 123-130.*

(Continued)

*Primary Examiner* — Stephen Holwerda
(74) *Attorney, Agent, or Firm* — Norton Rose Fulbright US LLP

(57) ABSTRACT

A robot system for use in surgical procedures has two movable arms, each arm having a six of degrees of freedom of movement and an end effector which can be rolled about its axis and an actuator which can slide along the axis for operating different tools adapted to be supported by the end effector. Each end effector including optical force sensors for detecting forces applied to the tool by engagement with the part of the patient. The robot is MRI compatible and can be configured to operate within a closed magnet bore. The arms are driven about vertical and horizontal axes by piezoelectric motors.

16 Claims, 16 Drawing Sheets

(52) U.S. Cl.
CPC ......... *A61B19/5223* (2013.01); *A61B 19/5244* (2013.01); *A61B 19/54* (2013.01); *A61B 19/56* (2013.01); *A61B 2017/00911* (2013.01); *A61B 2019/223* (2013.01); *A61B 2019/2223* (2013.01); *A61B 2019/2234* (2013.01); *A61B 2019/2242* (2013.01); *A61B 2019/2269* (2013.01); *A61B 2019/2288* (2013.01); *A61B 2019/2292* (2013.01); *A61B 2019/2296* (2013.01); *A61B 2019/464* (2013.01); *A61B 2019/502* (2013.01); *A61B 2019/5236* (2013.01); *A61B 2019/5259* (2013.01); *A61B 2019/5287* (2013.01)

(56) References Cited

U.S. PATENT DOCUMENTS

| | | | | |
|---|---|---|---|---|
| 3,818,154 | A | 6/1974 | Presentey | 200/6 A |
| 3,923,166 | A | 12/1975 | Fletcher et al. | 414/4 |
| 4,068,156 | A | 1/1978 | Johnson et al. | 318/575 |
| 4,239,431 | A | 12/1980 | Davini | 414/1 |
| 4,252,360 | A | 2/1981 | Gallaher | 414/732 |
| 4,283,165 | A | 8/1981 | Vertut | 414/733 |
| 4,300,198 | A | 11/1981 | Davini | 700/264 |
| 4,598,311 | A | 7/1986 | Bellina | 348/79 |
| 4,600,357 | A | 7/1986 | Coules | 414/730 |
| 4,636,137 | A | 1/1987 | Lemelson | 414/730 |
| 4,686,698 | A | 8/1987 | Tompkins et al. | 348/230.1 |
| 4,704,915 | A | 11/1987 | Friesen et al. | 74/471 XY |
| 4,706,120 | A | 11/1987 | Slaughter et al. | 348/114 |
| 4,722,056 | A | 1/1988 | Roberts et al. | 606/130 |
| 4,736,826 | A | 4/1988 | White et al. | 191/12.2 A |
| 4,758,692 | A | 7/1988 | Roeser et al. | 200/6 A |
| 4,766,775 | A | 8/1988 | Hodge | 74/490.01 |
| 4,776,230 | A | 10/1988 | Susnjara | 74/490.01 |
| 4,791,934 | A | 12/1988 | Brunnett | 600/429 |
| 4,990,839 | A | 2/1991 | Schonlau | 700/248 |
| 4,993,912 | A | 2/1991 | King et al. | 414/729 |
| 5,004,457 | A | 4/1991 | Wyatt et al. | 604/158 |
| 5,006,122 | A | 4/1991 | Wyatt et al. | 606/130 |
| 5,038,089 | A | 8/1991 | Szakaly | 701/23 |
| 5,047,701 | A | 9/1991 | Takarada et al. | 700/246 |
| 5,053,975 | A | 10/1991 | Tsuchihashi et al. | 700/264 |
| 5,078,140 | A | 1/1992 | Kwoh | 600/417 |
| 5,086,401 | A | 2/1992 | Glassman et al. | 700/257 |
| 5,094,241 | A | 3/1992 | Allen | 600/426 |
| 5,116,180 | A | 5/1992 | Fung et al. | 414/5 |
| 5,142,931 | A | 9/1992 | Menahem | 74/471 XY |
| 5,177,563 | A | 1/1993 | Everett et al. | 356/621 |
| 5,184,601 | A | 2/1993 | Putman | 600/102 |
| 5,187,796 | A | 2/1993 | Wang et al. | 712/4 |
| 5,223,776 | A | 6/1993 | Radke et al. | 318/568.1 |
| 5,227,707 | A | 7/1993 | Mitomi et al. | 318/568.1 |
| 5,251,127 | A | 10/1993 | Raab | 606/130 |
| 5,265,486 | A | 11/1993 | Hartman et al. | 74/416 |
| 5,279,309 | A | 1/1994 | Taylor et al. | 600/595 |
| 5,299,288 | A | 3/1994 | Glassman et al. | 700/245 |
| 5,305,203 | A | 4/1994 | Raab | 606/1 |
| 5,305,652 | A | 4/1994 | Zimmer | 74/490.01 |
| 5,332,013 | A | 7/1994 | Sugita et al. | 141/98 |
| 5,343,385 | A | 8/1994 | Joskowicz et al. | 700/57 |
| 5,343,391 | A | 8/1994 | Mushabac | 433/76 |
| 5,347,616 | A | 9/1994 | Minami | 700/251 |
| 5,350,355 | A * | 9/1994 | Sklar | 604/23 |
| 5,351,676 | A | 10/1994 | Putman | 600/117 |
| 5,368,015 | A | 11/1994 | Wilk | 600/104 |
| 5,371,836 | A | 12/1994 | Mitomi et al. | 700/245 |
| 5,382,885 | A | 1/1995 | Salcudean et al. | 318/568.11 |
| 5,383,454 | A | 1/1995 | Bucholz | 600/429 |
| 5,389,101 | A | 2/1995 | Heilbrun et al. | 606/130 |
| 5,389,865 | A | 2/1995 | Jacobus et al. | 318/568.11 |
| 5,397,323 | A | 3/1995 | Taylor et al. | 606/130 |
| 5,402,801 | A | 4/1995 | Taylor | 128/898 |
| 5,408,409 | A | 4/1995 | Glassman et al. | 600/407 |
| 5,413,454 | A | 5/1995 | Movsesian | 414/729 |
| 5,417,210 | A | 5/1995 | Funda et al. | 600/425 |
| 5,441,505 | A | 8/1995 | Nakamura | 606/130 |
| 5,445,166 | A | 8/1995 | Taylor | 128/897 |
| 5,459,382 | A | 10/1995 | Jacobus et al. | 318/568.11 |
| 5,486,185 | A * | 1/1996 | Freitas et al. | 606/142 |
| 5,494,034 | A | 2/1996 | Schlondorff et al. | 600/425 |
| 5,515,478 | A | 5/1996 | Wang | 700/251 |
| 5,524,180 | A | 6/1996 | Wang et al. | 600/118 |
| 5,541,622 | A | 7/1996 | Engle et al. | 345/161 |
| 5,542,028 | A | 7/1996 | Minami | 700/251 |
| 5,553,198 | A | 9/1996 | Wang et al. | 700/245 |
| 5,562,012 | A | 10/1996 | Nishi et al. | 74/490.01 |
| 5,570,992 | A | 11/1996 | Lemelson | 414/744.3 |
| 5,572,999 | A | 11/1996 | Funda et al. | 600/118 |
| 5,624,398 | A | 4/1997 | Smith et al. | 604/95.01 |
| 5,628,315 | A | 5/1997 | Vilsmeier et al. | 600/426 |
| 5,629,594 | A | 5/1997 | Jacobus et al. | 318/568.11 |
| 5,630,431 | A | 5/1997 | Taylor | 128/897 |
| 5,642,805 | A | 7/1997 | Tefft | 200/43.08 |
| 5,643,268 | A | 7/1997 | Vilsmeier | 606/308 |
| 5,647,554 | A | 7/1997 | Ikegami et al. | 242/390.9 |
| 5,657,429 | A | 8/1997 | Wang et al. | 700/251 |
| 5,682,886 | A | 11/1997 | Delp et al. | 600/407 |
| 5,682,890 | A | 11/1997 | Kormos et al. | 600/417 |
| 5,691,898 | A | 11/1997 | Rosenberg et al. | 700/85 |
| D387,427 | S | 12/1997 | Bucholz et al. | 24/140 |
| 5,695,500 | A | 12/1997 | Taylor et al. | 606/130 |
| 5,695,501 | A | 12/1997 | Carol et al. | 606/130 |
| 5,702,406 | A | 12/1997 | Vilsmeier et al. | 606/130 |
| 5,710,870 | A | 1/1998 | Ohm et al. | 700/263 |
| 5,735,278 | A | 4/1998 | Hoult et al. | 128/653.2 |
| 5,748,767 | A | 5/1998 | Raab | 382/128 |
| 5,749,362 | A | 5/1998 | Funda et al. | 600/407 |
| 5,754,741 | A | 5/1998 | Wang et al. | 700/251 |
| 5,762,458 | A | 6/1998 | Wang et al. | 414/1 |
| 5,766,126 | A | 6/1998 | Anderson | 600/102 |
| 5,769,861 | A | 6/1998 | Vilsmeier | 606/130 |
| 5,781,705 | A | 7/1998 | Endo | 700/262 |
| 5,784,542 | A | 7/1998 | Ohm et al. | 700/260 |
| 5,792,135 | A * | 8/1998 | Madhani et al. | 606/1 |
| 5,794,621 | A | 8/1998 | Hogan et al. | 600/407 |
| 5,797,900 | A | 8/1998 | Madhani et al. | 606/1 |
| 5,797,924 | A | 8/1998 | Schulte et al. | 606/130 |
| 5,799,055 | A | 8/1998 | Peshkin et al. | 378/42 |
| 5,800,423 | A | 9/1998 | Jensen | 606/1 |
| 5,807,377 | A | 9/1998 | Madhani et al. | 606/1 |
| 5,815,640 | A | 9/1998 | Wang et al. | 700/251 |
| 5,817,084 | A * | 10/1998 | Jensen | 606/1 |
| 5,820,623 | A | 10/1998 | Ng | 606/1 |
| 5,823,960 | A | 10/1998 | Young et al. | 600/415 |
| 5,828,813 | A | 10/1998 | Ohm | 700/260 |
| 5,841,950 | A | 11/1998 | Wang et al. | 700/264 |
| 5,851,183 | A | 12/1998 | Bucholz | 600/425 |
| 5,855,583 | A | 1/1999 | Wang et al. | 606/139 |
| 5,868,675 | A | 2/1999 | Henrion et al. | 600/424 |
| 5,871,018 | A | 2/1999 | Delp et al. | 128/898 |
| 5,871,445 | A | 2/1999 | Bucholz | 600/407 |
| 5,876,325 | A | 3/1999 | Mizuno et al. | 600/102 |
| 5,878,193 | A | 3/1999 | Wang et al. | 700/251 |
| 5,887,121 | A | 3/1999 | Funda et al. | 700/263 |
| 5,889,507 | A | 3/1999 | Engle et al. | 345/161 |
| 5,891,034 | A | 4/1999 | Bucholz | 600/426 |
| 5,907,487 | A | 5/1999 | Rosenberg et al. | 700/85 |
| 5,907,664 | A | 5/1999 | Wang et al. | 700/251 |
| 5,911,036 | A | 6/1999 | Wright et al. | 700/259 |
| 5,943,914 | A | 8/1999 | Morimoto et al. | 74/479.01 |
| 5,950,629 | A | 9/1999 | Taylor et al. | 128/897 |
| 5,953,196 | A | 9/1999 | Zimmermann | 361/144 |
| 5,970,499 | A | 10/1999 | Smith et al. | 707/104.1 |
| 5,971,976 | A | 10/1999 | Wang et al. | 606/1 |
| 5,971,997 | A | 10/1999 | Guthrie et al. | 606/130 |
| 5,976,156 | A | 11/1999 | Taylor et al. | 606/130 |
| 6,000,297 | A | 12/1999 | Morimoto et al. | 74/479.01 |
| 6,001,108 | A | 12/1999 | Wang et al. | 606/130 |
| 6,006,127 | A | 12/1999 | Van Der Brug et al. | 600/427 |
| 6,007,550 | A | 12/1999 | Wang et al. | 606/139 |
| 6,010,476 | A * | 1/2000 | Saadat | 604/22 |
| 6,013,087 | A | 1/2000 | Adams et al. | 606/130 |
| 6,016,607 | A | 1/2000 | Morimoto et al. | 33/1 M |

(56) References Cited

U.S. PATENT DOCUMENTS

| | | | |
|---|---|---|---|
| 6,024,695 A | 2/2000 | Taylor et al. | 600/102 |
| 6,033,415 A | 3/2000 | Mittelstadt et al. | 606/130 |
| 6,035,228 A | 3/2000 | Yanof et al. | 600/429 |
| 6,052,611 A | 4/2000 | Yanof et al. | 600/429 |
| 6,063,095 A | 5/2000 | Wang et al. | 606/139 |
| 6,069,932 A | 5/2000 | Peshkin et al. | 378/42 |
| 6,083,163 A | 7/2000 | Wegner et al. | 600/429 |
| 6,096,004 A * | 8/2000 | Meglan et al. | 604/95.01 |
| 6,102,850 A | 8/2000 | Wang et al. | 600/102 |
| 6,104,158 A | 8/2000 | Jacobus et al. | 318/568.11 |
| 6,106,511 A | 8/2000 | Jensen | 606/1 |
| 6,132,368 A | 10/2000 | Cooper | 600/102 |
| 6,132,441 A | 10/2000 | Grace | 606/147 |
| 6,149,592 A | 11/2000 | Yanof et al. | 600/427 |
| 6,167,292 A | 12/2000 | Badano et al. | 600/407 |
| 6,178,345 B1 | 1/2001 | Vilsmeier et al. | 600/425 |
| 6,184,868 B1 | 2/2001 | Shahoian et al. | 345/161 |
| 6,197,017 B1 | 3/2001 | Brock et al. | 606/1 |
| 6,201,984 B1 | 3/2001 | Funda et al. | 600/407 |
| 6,205,411 B1 | 3/2001 | DiGioia et al. | 703/11 |
| 6,223,067 B1 | 4/2001 | Vilsmeier et al. | 600/426 |
| 6,226,566 B1 | 5/2001 | Funda et al. | 700/263 |
| 6,231,526 B1 | 5/2001 | Taylor et al. | 600/587 |
| 6,233,504 B1 | 5/2001 | Das et al. | 700/260 |
| 6,234,045 B1 | 5/2001 | Kaiser | 74/572.2 |
| 6,235,038 B1 | 5/2001 | Hunter et al. | 606/130 |
| 6,236,875 B1 | 5/2001 | Bucholz et al. | 600/407 |
| 6,238,384 B1 | 5/2001 | Peer | 606/1 |
| 6,244,809 B1 | 6/2001 | Wang et al. | 414/1 |
| 6,246,200 B1 * | 6/2001 | Blumenkranz et al. | 318/568.11 |
| 6,271,833 B1 | 8/2001 | Rosenberg et al. | 345/161 |
| RE37,374 E | 9/2001 | Roston et al. | 318/561 |
| 6,292,713 B1 | 9/2001 | Jouppi et al. | 700/245 |
| 6,298,262 B1 | 10/2001 | Franck et al. | 600/426 |
| 6,312,435 B1 | 11/2001 | Wallace et al. | 606/130 |
| 6,322,567 B1 | 11/2001 | Mittelstadt et al. | 606/130 |
| 6,323,842 B1 | 11/2001 | Krukovsky | 345/163 |
| 6,331,181 B1 | 12/2001 | Tierney et al. | 606/130 |
| 6,347,240 B1 | 2/2002 | Foley et al. | 600/426 |
| 6,348,911 B1 | 2/2002 | Rosenberg et al. | 345/161 |
| 6,348,912 B1 | 2/2002 | Smith | 345/163 |
| 6,349,245 B1 | 2/2002 | Finlay | 700/245 |
| 6,351,659 B1 | 2/2002 | Vilsmeier | 600/407 |
| 6,359,614 B1 | 3/2002 | McVicar | 345/161 |
| 6,364,888 B1 | 4/2002 | Niemeyer et al. | 606/130 |
| 6,379,302 B1 | 4/2002 | Kessman et al. | 600/437 |
| 6,385,509 B2 | 5/2002 | Das et al. | 700/260 |
| 6,393,340 B2 | 5/2002 | Funda et al. | 700/263 |
| 6,394,998 B1 | 5/2002 | Wallace et al. | 606/1 |
| 6,398,726 B1 | 6/2002 | Ramans et al. | 600/229 |
| 6,400,979 B1 | 6/2002 | Stoianovici et al. | 600/427 |
| 6,409,735 B1 | 6/2002 | Andre et al. | 606/130 |
| 6,424,856 B1 | 7/2002 | Vilsmeier et al. | 600/426 |
| 6,424,885 B1 | 7/2002 | Niemeyer et al. | 700/245 |
| 6,428,547 B1 | 8/2002 | Vilsmeier et al. | 606/130 |
| 6,432,112 B2 | 8/2002 | Brock et al. | 606/130 |
| 6,434,416 B1 | 8/2002 | Mizoguchi et al. | 600/427 |
| 6,436,107 B1 | 8/2002 | Wang et al. | 606/139 |
| 6,441,577 B2 | 8/2002 | Blumenkranz et al. | 318/568.11 |
| 6,451,027 B1 | 9/2002 | Cooper et al. | 606/130 |
| 6,459,926 B1 | 10/2002 | Nowlin et al. | 600/429 |
| 6,463,361 B1 | 10/2002 | Wang et al. | 700/258 |
| 6,470,236 B2 | 10/2002 | Ohtsuki | 700/247 |
| 6,490,467 B1 | 12/2002 | Bucholz et al. | 600/407 |
| 6,491,691 B1 | 12/2002 | Morley et al. | 606/49 |
| 6,491,699 B1 | 12/2002 | Henderson et al. | 606/130 |
| 6,493,608 B1 | 12/2002 | Niemeyer | 700/302 |
| 6,496,099 B2 | 12/2002 | Wang et al. | 340/3.7 |
| 6,516,046 B1 | 2/2003 | Frohlich et al. | 378/65 |
| 6,522,906 B1 | 2/2003 | Salisbury et al. | 600/407 |
| 6,522,949 B1 | 2/2003 | Ikeda et al. | 700/245 |
| 6,527,443 B1 | 3/2003 | Vilsmeier et al. | 378/205 |
| 6,546,277 B1 | 4/2003 | Franck et al. | 600/426 |
| 6,547,782 B1 | 4/2003 | Taylor | 606/14 |
| 6,551,325 B2 | 4/2003 | Neubauer et al. | 606/88 |
| 6,554,844 B2 | 4/2003 | Lee et al. | 606/130 |
| 6,561,993 B2 | 5/2003 | Adapathya et al. | 600/595 |
| 6,565,554 B1 | 5/2003 | Niemeyer | 606/1 |
| 6,574,355 B2 | 6/2003 | Green | 382/128 |
| 6,584,174 B2 | 6/2003 | Schubert et al. | 378/165 |
| 6,587,750 B2 | 7/2003 | Gerbi et al. | 700/245 |
| 6,590,171 B1 | 7/2003 | Wolf et al. | 200/51 LM |
| 6,594,552 B1 | 7/2003 | Nowlin et al. | 700/260 |
| 6,597,971 B2 | 7/2003 | Kanno | 700/245 |
| 6,609,022 B2 | 8/2003 | Vilsmeier et al. | 600/426 |
| 6,620,173 B2 | 9/2003 | Gerbi et al. | 606/130 |
| 6,639,789 B2 | 10/2003 | Beger | 361/681 |
| 6,642,686 B1 | 11/2003 | Ruch | 318/568.21 |
| 6,645,196 B1 | 11/2003 | Nixon et al. | 606/1 |
| 6,646,541 B1 | 11/2003 | Wang et al. | 340/3.54 |
| 6,659,939 B2 | 12/2003 | Moll et al. | 600/102 |
| 6,661,571 B1 | 12/2003 | Shioda et al. | 359/372 |
| 6,669,686 B1 * | 12/2003 | Singh | 606/12 |
| 6,675,069 B2 | 1/2004 | Uratani | 700/245 |
| 6,675,070 B2 | 1/2004 | Lapham | 700/245 |
| 6,676,669 B2 | 1/2004 | Charles et al. | 606/130 |
| 6,676,684 B1 | 1/2004 | Morley et al. | 606/205 |
| 6,678,583 B2 | 1/2004 | Nasr et al. | 700/245 |
| 6,681,151 B1 | 1/2004 | Weinzimmer et al. | 700/259 |
| 6,684,129 B2 | 1/2004 | Salisbury et al. | 700/245 |
| 6,685,698 B2 | 2/2004 | Morley et al. | 606/1 |
| 6,690,999 B2 | 2/2004 | Kimura | 700/245 |
| 6,694,162 B2 | 2/2004 | Hartlep | 600/378 |
| 6,694,164 B2 | 2/2004 | Glossop | 600/407 |
| 6,695,786 B2 | 2/2004 | Wang et al. | 600/461 |
| 6,697,044 B2 | 2/2004 | Shahoian et al. | 345/156 |
| 6,699,177 B1 | 3/2004 | Wang et al. | 600/102 |
| 6,702,805 B1 | 3/2004 | Stuart | 606/1 |
| 6,708,184 B2 | 3/2004 | Smith et al. | 707/104.1 |
| 6,714,629 B2 | 3/2004 | Vilsmeier | 378/165 |
| 6,714,839 B2 | 3/2004 | Salisbury et al. | 700/245 |
| 6,720,988 B1 | 4/2004 | Gere et al. | 348/45 |
| 6,722,053 B2 | 4/2004 | Henry et al. | 34/69 |
| 6,723,106 B1 | 4/2004 | Charles et al. | 606/130 |
| 6,724,922 B1 | 4/2004 | Vilsmeier | 382/128 |
| 6,725,078 B2 | 4/2004 | Bucholz et al. | 600/410 |
| 6,728,599 B2 | 4/2004 | Wang et al. | 700/258 |
| 6,730,021 B2 | 5/2004 | Vassiliades, Jr. et al. | 600/202 |
| 6,731,988 B1 | 5/2004 | Green | 700/3 |
| 6,746,443 B1 | 6/2004 | Morley et al. | 606/1 |
| 6,748,298 B2 | 6/2004 | Heiligensetzer | 700/260 |
| 6,755,338 B2 | 6/2004 | Hahnen et al. | 227/175.1 |
| 6,757,586 B2 | 6/2004 | Milojevic et al. | 700/245 |
| 6,758,843 B2 | 7/2004 | Jensen | 606/1 |
| 6,763,284 B2 | 7/2004 | Watanabe et al. | 700/264 |
| 6,766,204 B2 | 7/2004 | Niemeyer et al. | 700/1 |
| 6,772,002 B2 | 8/2004 | Schmidt et al. | 600/429 |
| 6,772,053 B2 | 8/2004 | Niemeyer | 700/302 |
| 6,776,526 B2 | 8/2004 | Zeiss | 378/207 |
| 6,781,569 B1 | 8/2004 | Gregorio et al. | 345/157 |
| 6,783,524 B2 | 8/2004 | Anderson et al. | 606/28 |
| 6,785,572 B2 | 8/2004 | Yanof et al. | 600/427 |
| 6,785,593 B2 | 8/2004 | Wang et al. | 700/258 |
| 6,786,896 B1 | 9/2004 | Madhani et al. | 606/1 |
| 6,788,018 B1 | 9/2004 | Blumenkranz | 318/568.11 |
| 6,788,999 B2 | 9/2004 | Green | 700/275 |
| 6,793,653 B2 | 9/2004 | Sanchez et al. | 606/1 |
| 6,799,065 B1 | 9/2004 | Niemeyer | 600/407 |
| 6,799,088 B2 | 9/2004 | Wang et al. | 700/258 |
| 6,801,008 B1 | 10/2004 | Jacobus et al. | 318/568.11 |
| 6,804,547 B2 | 10/2004 | Pelzer et al. | 600/424 |
| 6,810,281 B2 | 10/2004 | Brock et al. | 600/427 |
| 6,816,755 B2 | 11/2004 | Habibi et al. | 700/259 |
| 6,817,972 B2 | 11/2004 | Snow | 600/37 |
| 6,817,974 B2 | 11/2004 | Cooper et al. | 600/142 |
| 6,827,712 B2 | 12/2004 | Tovey et al. | 606/1 |
| 6,830,174 B2 | 12/2004 | Hillstead et al. | 227/175.1 |
| 6,836,700 B2 | 12/2004 | Greene et al. | 606/1 |
| 6,836,703 B2 | 12/2004 | Wang et al. | 700/258 |
| 6,837,883 B2 | 1/2005 | Moll et al. | 606/1 |
| 6,839,612 B2 | 1/2005 | Sanchez et al. | 700/245 |
| 6,840,938 B1 | 1/2005 | Morley et al. | 606/51 |
| 6,843,793 B2 | 1/2005 | Brock et al. | 606/130 |
| 6,845,295 B2 | 1/2005 | Cheng et al. | 700/245 |

(56) References Cited

U.S. PATENT DOCUMENTS

| | | | |
|---|---|---|---|
| 6,845,296 B2 | 1/2005 | Ban et al. | 700/245 |
| 6,850,817 B1 | 2/2005 | Green | 700/245 |
| 6,852,107 B2 | 2/2005 | Wang et al. | 606/1 |
| 6,853,856 B2 | 2/2005 | Yanof et al. | 600/417 |
| 6,860,878 B2 | 3/2005 | Brock | 606/1 |
| 6,865,253 B2 | 3/2005 | Blumhofer et al. | 378/65 |
| 6,865,411 B2 | 3/2005 | Erbel et al. | 600/407 |
| 6,866,671 B2 | 3/2005 | Tierney | 606/130 |
| 6,871,117 B2 | 3/2005 | Wang et al. | 700/245 |
| 6,873,867 B2 | 3/2005 | Vilsmeier | 600/415 |
| 6,879,880 B2 | 4/2005 | Nowlin et al. | 700/260 |
| 6,889,073 B2 | 5/2005 | Lampman et al. | 600/422 |
| 6,889,116 B2 | 5/2005 | Jinno | 700/245 |
| 6,892,112 B2 | 5/2005 | Wang et al. | 700/258 |
| 6,898,484 B2 | 5/2005 | Lemelson et al. | 700/245 |
| 6,899,705 B2 | 5/2005 | Niemeyer | 606/1 |
| 6,905,460 B2 | 6/2005 | Wang et al. | 600/102 |
| 6,905,491 B1 | 6/2005 | Wang et al. | 606/1 |
| 6,907,318 B2 | 6/2005 | Passmore et al. | 700/245 |
| 6,911,916 B1 | 6/2005 | Wang et al. | 340/825 |
| 6,925,357 B2 | 8/2005 | Wang et al. | 700/245 |
| 6,928,490 B1 | 8/2005 | Bucholz et al. | 709/249 |
| 6,933,695 B2 | 8/2005 | Blumenkranz | 318/568.11 |
| 6,936,001 B1 | 8/2005 | Snow | 600/37 |
| 6,948,398 B2 | 9/2005 | Dybro | 74/471 XY |
| 6,949,106 B2 | 9/2005 | Brock et al. | 606/130 |
| 6,951,535 B2 | 10/2005 | Ghodoussi et al. | 600/101 |
| 6,963,792 B1 | 11/2005 | Green | 700/251 |
| 6,965,812 B2 | 11/2005 | Wang et al. | 700/258 |
| 6,968,224 B2 | 11/2005 | Kessman et al. | 600/407 |
| 6,974,449 B2 | 12/2005 | Niemeyer | 606/1 |
| 6,985,766 B2 | 1/2006 | Braun et al. | 600/424 |
| 6,987,504 B2 | 1/2006 | Rosenberg et al. | 345/156 |
| 6,994,703 B2 | 2/2006 | Wang et al. | 606/10 |
| 6,996,456 B2 | 2/2006 | Cordell et al. | 700/258 |
| 6,999,852 B2 | 2/2006 | Green | 700/245 |
| 7,006,895 B2 | 2/2006 | Green | 700/245 |
| 7,018,386 B2 | 3/2006 | Nakamura | 606/130 |
| 7,023,423 B2 | 4/2006 | Rosenberg | 345/161 |
| 7,025,064 B2 | 4/2006 | Wang et al. | 128/898 |
| 7,025,761 B2 | 4/2006 | Wang et al. | 606/1 |
| 7,027,892 B2 | 4/2006 | Wang et al. | 700/245 |
| 7,035,716 B2 | 4/2006 | Harris et al. | 700/245 |
| 7,039,500 B2 | 5/2006 | Milojevic et al. | 700/245 |
| 7,043,338 B2 | 5/2006 | Jinno | 700/245 |
| 7,046,765 B2 | 5/2006 | Wong et al. | 378/117 |
| 7,048,745 B2 | 5/2006 | Tierney et al. | 606/130 |
| 7,063,479 B2 | 6/2006 | Chinzei | 403/46 |
| 7,074,179 B2 | 7/2006 | Wang et al. | 600/101 |
| 7,076,286 B2 | 7/2006 | Mizoguchi et al. | 600/476 |
| 7,083,571 B2 | 8/2006 | Wang et al. | 600/102 |
| 7,107,124 B2 | 9/2006 | Green | 700/245 |
| 7,155,316 B2 | 12/2006 | Sutherland et al. | 700/248 |
| 2001/0000663 A1 | 5/2001 | Shahoian et al. | 345/156 |
| 2001/0008599 A1 | 7/2001 | Chinzei | 403/56 |
| 2001/0012932 A1 | 8/2001 | Peer | 606/1 |
| 2001/0013764 A1 | 8/2001 | Blumenkranz et al. | 318/568.11 |
| 2001/0018591 A1 | 8/2001 | Brock et al. | 606/130 |
| 2001/0025183 A1 | 9/2001 | Shahidi | 606/130 |
| 2001/0037064 A1 | 11/2001 | Shahidi | 600/429 |
| 2002/0032451 A1 | 3/2002 | Tierney et al. | 606/130 |
| 2002/0032452 A1 | 3/2002 | Tierney et al. | 606/130 |
| 2002/0038084 A1 | 3/2002 | Pelzer et al. | 600/407 |
| 2002/0038116 A1 | 3/2002 | Lee et al. | 606/1 |
| 2002/0042620 A1 | 4/2002 | Julian et al. | 606/130 |
| 2002/0045888 A1 | 4/2002 | Ramans et al. | 606/1 |
| 2002/0058929 A1 | 5/2002 | Green | 606/205 |
| 2002/0072736 A1 | 6/2002 | Tierney et al. | 606/1 |
| 2002/0082612 A1 | 6/2002 | Moll et al. | 606/130 |
| 2002/0091374 A1 | 7/2002 | Cooper | 606/1 |
| 2002/0103476 A1 | 8/2002 | Madhani et al. | 606/1 |
| 2002/0111713 A1 | 8/2002 | Wang et al. | 700/245 |
| 2002/0120188 A1 | 8/2002 | Brock et al. | 600/407 |
| 2002/0120217 A1 | 8/2002 | Adapathya et al. | 600/595 |
| 2002/0120252 A1 | 8/2002 | Brock et al. | 606/1 |
| 2002/0120254 A1 | 8/2002 | Julian et al. | 606/1 |
| 2002/0120363 A1 | 8/2002 | Salisbury et al. | 700/254 |
| 2002/0126091 A1 | 9/2002 | Rosenberg et al. | 345/161 |
| 2002/0128633 A1 | 9/2002 | Brock et al. | 606/1 |
| 2002/0128661 A1 | 9/2002 | Brock et al. | 606/130 |
| 2002/0128662 A1 | 9/2002 | Brock et al. | 606/130 |
| 2002/0133173 A1 | 9/2002 | Brock et al. | 606/130 |
| 2002/0133174 A1 | 9/2002 | Charles et al. | 606/130 |
| 2002/0138082 A1 | 9/2002 | Brock et al. | 606/130 |
| 2002/0143319 A1 | 10/2002 | Brock | 606/1 |
| 2002/0165524 A1 | 11/2002 | Sanchez et al. | 606/1 |
| 2002/0177857 A1 | 11/2002 | Otsuka et al. | 606/130 |
| 2002/0186299 A1 | 12/2002 | Cofer | 375/259 |
| 2002/0188293 A1 | 12/2002 | Manzo | 606/45 |
| 2003/0018323 A1 | 1/2003 | Wallace et al. | 606/1 |
| 2003/0023191 A1 | 1/2003 | Tripp | 600/595 |
| 2003/0029463 A1 | 2/2003 | Niemeyer | 128/898 |
| 2003/0036748 A1 | 2/2003 | Cooper et al. | 606/1 |
| 2003/0040758 A1 | 2/2003 | Wang et al. | 606/130 |
| 2003/0045888 A1 | 3/2003 | Brock et al. | 606/130 |
| 2003/0050527 A1 | 3/2003 | Fox et al. | 600/13 |
| 2003/0050649 A1 | 3/2003 | Brock et al. | 606/130 |
| 2003/0050733 A1 | 3/2003 | Wang et al. | 700/245 |
| 2003/0055410 A1 | 3/2003 | Evans et al. | 606/1 |
| 2003/0060808 A1 | 3/2003 | Wilk | 606/1 |
| 2003/0060809 A1 | 3/2003 | Wang et al. | 606/1 |
| 2003/0065310 A1 | 4/2003 | Wang et al. | 606/1 |
| 2003/0065311 A1 | 4/2003 | Wang et al. | 606/1 |
| 2003/0083648 A1 | 5/2003 | Wang et al. | 606/1 |
| 2003/0083650 A1 | 5/2003 | Wang et al. | 606/10 |
| 2003/0083651 A1 | 5/2003 | Wang et al. | 606/10 |
| 2003/0083673 A1 | 5/2003 | Tierney et al. | 606/130 |
| 2003/0093129 A1 | 5/2003 | Nicolelis et al. | 607/45 |
| 2003/0100817 A1 | 5/2003 | Wang et al. | 600/102 |
| 2003/0109780 A1 | 6/2003 | Coste-Maniere et al. | 600/407 |
| 2003/0109877 A1 | 6/2003 | Morley et al. | 606/49 |
| 2003/0114962 A1 | 6/2003 | Niemeyer | 700/245 |
| 2003/0125716 A1 | 7/2003 | Wang et al. | 606/1 |
| 2003/0135203 A1 | 7/2003 | Wang et al. | 606/1 |
| 2003/0135204 A1 | 7/2003 | Lee et al. | 606/1 |
| 2003/0139733 A1 | 7/2003 | Wang et al. | 606/1 |
| 2003/0144649 A1 | 7/2003 | Ghodoussi et al. | 606/1 |
| 2003/0167061 A1 | 9/2003 | Schlegel et al. | 606/130 |
| 2003/0191455 A1 | 10/2003 | Sanchez et al. | 606/1 |
| 2003/0195660 A1 | 10/2003 | Wang et al. | 700/258 |
| 2003/0195662 A1 | 10/2003 | Wang et al. | 700/258 |
| 2003/0195663 A1 | 10/2003 | Wang et al. | 700/258 |
| 2003/0216715 A1 | 11/2003 | Moll et al. | 606/1 |
| 2003/0220541 A1 | 11/2003 | Salisbury et al. | 600/101 |
| 2004/0011154 A1 | 1/2004 | Dybro | 74/473.3 |
| 2004/0024385 A1 | 2/2004 | Stuart | 606/1 |
| 2004/0039485 A1 | 2/2004 | Niemeyer et al. | 700/245 |
| 2004/0049205 A1 | 3/2004 | Lee et al. | 606/130 |
| 2004/0077939 A1 | 4/2004 | Graumann | 600/424 |
| 2004/0106916 A1 | 6/2004 | Quaid et al. | 606/1 |
| 2004/0111183 A1 | 6/2004 | Sutherland et al. | 700/245 |
| 2004/0116906 A1 | 6/2004 | Lipow | 606/1 |
| 2004/0119682 A1 | 6/2004 | Levine et al. | 345/156 |
| 2004/0128026 A1 | 7/2004 | Harris et al. | 700/245 |
| 2004/0151218 A1 | 8/2004 | Branzoi et al. | 372/25 |
| 2004/0162564 A1 | 8/2004 | Charles et al. | 606/130 |
| 2004/0167515 A1 | 8/2004 | Peterson et al. | 606/49 |
| 2004/0176751 A1 | 9/2004 | Weitzner et al. | 606/1 |
| 2004/0186345 A1 | 9/2004 | Yang et al. | 600/102 |
| 2004/0242993 A1 | 12/2004 | Tajima | 600/417 |
| 2004/0243147 A1 | 12/2004 | Lipow | 606/130 |
| 2004/0243176 A1 | 12/2004 | Hahnen et al. | 606/205 |
| 2004/0261179 A1 | 12/2004 | Blumenkranz | 5/630 |
| 2004/0267254 A1 | 12/2004 | Manzo et al. | 606/39 |
| 2005/0016822 A1 | 1/2005 | Mowatt et al. | 200/6 A |
| 2005/0027397 A1 | 2/2005 | Niemeyer | 700/245 |
| 2005/0038416 A1 | 2/2005 | Wang et al. | 606/1 |
| 2005/0075536 A1 | 4/2005 | Otsuka et al. | 600/102 |
| 2005/0092122 A1 | 5/2005 | Markert et al. | 74/490.01 |
| 2005/0107680 A1 | 5/2005 | Kopf et al. | 600/407 |
| 2005/0119790 A1 | 6/2005 | Sanchez et al. | 700/245 |
| 2005/0128186 A1 | 6/2005 | Shahoian et al. | 345/161 |
| 2005/0154295 A1 | 7/2005 | Quistgaard et al. | 600/424 |
| 2005/0154493 A1 | 7/2005 | Wang et al. | 700/245 |

(56) References Cited

U.S. PATENT DOCUMENTS

| | | | |
|---|---|---|---|
| 2005/0166413 | A1 | 8/2005 | Crampton ........................ 33/503 |
| 2005/0174324 | A1 | 8/2005 | Liberty et al. ................ 345/156 |
| 2005/0183532 | A1 | 8/2005 | Najafi et al. ............... 74/490.01 |
| 2005/0195166 | A1 | 9/2005 | Cooper et al. ................ 345/161 |
| 2005/0200324 | A1 | 9/2005 | Guthart et al. ........... 318/568.11 |
| 2005/0204851 | A1 | 9/2005 | Morley et al. ............. 74/490.01 |
| 2005/0216033 | A1 | 9/2005 | Lee et al. ....................... 606/130 |
| 2005/0228365 | A1 | 10/2005 | Wang et al. ........................ 606/1 |
| 2005/0253806 | A1 | 11/2005 | Liberty et al. ................ 345/156 |
| 2006/0030840 | A1 | 2/2006 | Nowlin et al. ..................... 606/1 |
| 2006/0036264 | A1 | 2/2006 | Selover et al. ................ 606/130 |
| 2006/0047365 | A1 | 3/2006 | Ghodoussi et al. ........... 700/251 |
| 2006/0087746 | A1 | 4/2006 | Lipow ........................... 359/689 |
| 2006/0100642 | A1 | 5/2006 | Yang et al. .................... 606/130 |
| 2006/0106493 | A1 | 5/2006 | Niemeyer et al. ............. 700/245 |
| 2006/0122496 | A1 | 6/2006 | George et al. ................. 600/424 |
| 2006/0133572 | A1 | 6/2006 | Wong et al. ................... 378/117 |
| 2006/0133573 | A1 | 6/2006 | Wong et al. ................... 378/117 |
| 2006/0142657 | A1 | 6/2006 | Quaid et al. .................. 600/424 |
| 2006/0149418 | A1 | 7/2006 | Anvari ........................... 700/245 |
| 2006/0161136 | A1 | 7/2006 | Anderson et al. .................. 606/1 |
| 2006/0161137 | A1 | 7/2006 | Orban et al. ....................... 606/1 |
| 2006/0161138 | A1 | 7/2006 | Orban et al. ....................... 606/1 |

FOREIGN PATENT DOCUMENTS

| | | |
|---|---|---|
| WO | WO 93/13916 | 7/1993 |
| WO | WO 99/58055 | 11/1999 |
| WO | WO 00/33723 | 6/2000 |
| WO | WO 02/065933 | 8/2002 |

OTHER PUBLICATIONS

Chinzei et al., "MR compatible surgical assist robot: System integration and preliminary feasibility study," *Medical Image Computing and Computer-Assisted Intervention*, Third International Conference, MICCAI 2000, Pittsburg, PA, USA, Oct. 11-14, 2000, Scott L. Delp et al., Ed., pp. 921-930.

Masamune et al., "Development of an MRI-compatible needle insertion manipulator for stereotactic neurosurgery," *Journal of Image Guided Surgery*, 1:242-248, 1995.

U.S. Appl. No. 07/230,588, filed Aug. 10, 1988, Rabb.
U.S. Appl. No. 07/927,801, filed Aug. 10, 1992, Wang.
U.S. Appl. No. 08/005,604, filed Jan. 19, 1993, Wang.
U.S. Appl. No. 08/900,382, filed Jul. 12, 1997, Wang.
U.S. Appl. No. 60/082,013, filed Apr. 16, 1998, Boswell.
U.S. Appl. No. 60/095,303, filed Aug. 4, 1998, Blumenkranz.
U.S. Appl. No. 60/111,710, filed Dec. 8, 1998, Salibury.
U.S. Appl. No. 60/111,711, filed Dec. 8, 1998, Niemeyer.
U.S. Appl. No. 60/111,713, filed Dec. 8, 1998, Younge.
U.S. Appl. No. 60/111,714, filed Dec. 8, 1998, Gere.
U.S. Appl. No. 60/116,842, filed Jan. 22, 1999, Guthart.

Bate et al., "The feasibility of force control over the Internet," Internet, pp. 1-6, 2001.

Chiu et al., "3-D Visulaization for minimally invasive robotic coronary artery bypass (MIRCAB)," *Proc. 22nd Annual EMBS Int. Conf., IEEE*, 1728-1730, 2000.

Hayashibe et al., "Laser-pointing endoscope system for intra-operative 3D geometric registration," Internet, pp. 1-6, 2001.

Mack, "Minimally invasive and robotic surgery," Internet, pp. 568-572, 2001.

Vuskovic et al., "Realistic force feedback for virtual reality based diagnostic surgery," *IEEE*, pp. 1592-1598, 2000.

Notice of Allowance issued in U.S. Appl. No. 10/639,692, mailed Feb. 13, 2006.

Notice of Allowance issued in U.S. Appl. No. 11/480,701, mailed Oct. 17, 2007.

Notice of Allowance issued in U.S. Appl. No. 11/480,701, mailed Jan. 14, 2009.

Office Action issued in U.S. Appl. No. 10/639,692, mailed Jul. 27, 2005.

Office Action issued in U.S. Appl. No. 11/480,701, mailed Aug. 21, 2007.

Office Action issued in U.S. Appl. No. 11/480,701, mailed Jan. 16, 2007.

Office Action issued in U.S. Appl. No. 11/480,701, mailed Mar. 17, 2008.

Office Action issued in U.S. Appl. No. 12/027,043, mailed Mar. 30, 2009.

Response filed in U.S. Appl. No. 10/639,692, filed Nov. 28, 2005.
Response filed in U.S. Appl. No. 11/480,701, filed Aug. 19, 2008.
Response filed in U.S. Appl. No. 11/480,701, filed Dec. 24, 2008.
Response filed in U.S. Appl. No. 11/480,701, filed Jul. 16, 2007.
Response filed in U.S. Appl. No. 12/027,043, filed Jul. 30, 2009.

Office Action issued in U.S. Appl. No. 11/562,768, mailed Jun. 10, 2009.

Notice of Allowance issued in U.S. Appl. No. 11/480,701, mailed May 7, 2009.

Sutherland et al., "Neuroarm: An MR Compatible Robot for Microsurgery," *Computer Assisted Radiology and Surgery* 1256: 504-508, 2003.

Black et al., "Development and Implementation of Intraoperative Magnetic Resonance Imaging and its Neurosurgical Applications," *Neurosurgery* 41:4 831-845.

Chiu et al. "3-D Guidance for Minimally Invasive Robotic Coronary Artery Bypass" *The Heart Surgery Forum #2000-9732*, 3(3):224-231, 2000.

Dohrmann et al., "History of Intraoperative Ultrasound in Neurosurgery," *Neurosurgery Clinics of North America*, 12:1, 155-165, 2001.

Grunert et al., "Basic Principles and Clinical Applications of Neuronavigation and Intraoperative Computed Tomography," *Computer Aided Surgery*, 3:166-173, 1998.

Henri et al., "Multimodality Image Integration for Sterotactic Surgical Planning," *Med. Phys.* 18:2, 167-177, 1991.

Peters, "Image-guided surgery: From X-rays to Virtual Reality," *Computer Methods in Biomechanics and Biomedical Engineering*, 4:27-57, 2000.

Sutherland et al., A Mobil High-Field Magnetic Resonance System for Neurosurgery, *J. Neurosurg.*, 91:804-813, 1999.

Sutherland et al., "Neurosurgical Suite of the Future III," *Neurosurgery Clinics of North America*,11:4, 593-609, 2001.

Notice of Allowance issued in U.S. Appl. No. 11/480,701, mailed Aug. 14, 2009.

Response to Office Action in U.S. Appl. No. 11/562,768 dated Dec. 10, 2009.

Office Action issued in U.S. Appl. No. 11/562,768 dated May 24, 2010.

Response to Office Action in U.S. Appl. No. 11/562,768 dated Nov. 26, 2010.

Office Action issued in U.S. Appl. No. 11/562,768 dated Feb. 24, 2011.

Office Action issued in U.S. Appl. No. 12/027,043 dated Nov. 3, 2009.

Response to Office Action in U.S. Appl. No. 12/027,043 dated Jan. 4, 2010.

Office Action issued in U.S. Appl. No. 12/027,043 dated Feb. 25, 2010, Mar. 25, 2010.

Response to Office Action in U.S. Appl. No. 12/027,043 dated Jul. 26, 2010.

Office Action issued in U.S. Appl. No. 12/027,043 dated Oct. 6, 2010.
Response to Office Action in U.S. Appl. No. 12/027,043 dated Jan. 6, 2011.

\* cited by examiner

MICROSURGICAL ROBOT SYSTEM

CROSS REFERENCES TO RELATED APPLICATIONS

This patent application is a continuation of co-pending application Ser. No. 11/562,768 filed on Nov. 22, 2006, which is a continuation of application Ser. No. 10/639,692 filed on Aug. 13, 2003, now U.S. Pat. No. 7,155,316, which claims priority to U.S. Provisional Patent Application No. 60/402,724 filed on Aug. 13, 2002; each of these applications is incorporated by reference in its entirety. This patent application is also co-pending with application Ser. No. 11/480,701 filed on Jul. 3, 2006.

BACKGROUND OF THE INVENTION

Complication avoidance in microsurgery (neurosurgery, ophthalmology, otorhinolaryngology, limb and digit reattachment) is crucial, and minimizes patient morbidity and health care costs. Current operative techniques rely on human surgeons, who have variable skill and dexterity. They also have physiological limits to their precision, tactile sensibility and stamina. Furthermore, the precise localization of brain pathology and neural structures is often difficult to achieve during surgery due to brain shifts and deformations as the operation progresses. While Intra-operative Magnetic Resonance Imaging (iMRI) has been used to monitor brain deformations, the surgeon currently has no effective way to use the iMRI data to enhance the precision and dexterity of surgery. They are compelled to rely on old techniques, and do not take advantage of these exquisite, updated images. Consequently, the quality of the surgery and outcomes is variable, and too often sub-optimal.

Surgical robots have the potential to increase the consistency and quality of neurosurgery, and when used in conjunction with the advanced diagnostic imaging capabilities of iMRI, can offer dramatic improvements. Unfortunately, there are no surgical robots that provide the surgeon with an ambidextrous and precise surgical system that uses updated iMRI patient data to achieve accurate image-guided surgery. In addition, there is no surgical robot with force sensing technology that is compatible with MRI systems.

Traditional surgery relies on the physician's surgical skills and dexterity and ability to localize structures in the body. Surgical robots have recently been developed to address the physical human issues such as fatigue and tremor in procedures. These systems were specifically developed for Minimally Invasive Surgery (MIS) or "key-hole" general surgery, orthopaedics and stereotactic neurosurgery.

The Intuitive Surgical Inc. DA VINCI® and Computer Motion ZEUS® robots are examples of MIS robots. MIS robots are not suitable for neurosurgery since they require a portal in the body and lack the required dexterity and ability to reposition to different surgical worksites. Furthermore, neither system is MR compatible nor is there any force feedback capability. One patent on this development is U.S. Pat. No. 6,394,998 of Wallace et al issued May 28, 2002.

The DA VINCI® system is archetypal for general surgical robots. It has an articulated ENDOWRIST®, at the end of its two 7 mm diameter 'working' arms. A more stable camera arm with two lenses (allowing stereoscopic images) is also inserted through an 8 mm portal. The end-effectors can manipulate instruments with tips as small as 2 mm. They have seven degrees of freedom (three at the wrist). The surgeon controls the robot through a console placed in the operating room, allowing control of both the external and internal surgical environments. The surgeon's interface has instrument controllers that can filter tremor and decrease the scale of motion. Foot pedals expand the surgeon's repertoire, allowing tissue coagulation and irrigation. Visual feedback is through a proprietary stereoscopic display, called Surgical Immersion™. FDA approval has been obtained for thoracoscopic, dominal and prostate procedures. Over one hundred DA VINCI® systems have been sold, and have been used to perform cholecystectomies, Nissen fundoplications, adrenalectomies, nephrectomies, mitral valve repairs, coronary artery bypass grafting and prostatectomies.

Surgical robots in orthopaedics may be classified as positioning or machining aids. ROBODOC®, used for hip replacement surgery, is an example of the latter. Again, they lack the dexterity, MR compatibility and force sensing needed for neurosurgery. The first-generation ROBODOC® was developed by IBM and the University of California Davis campus. The system was initially tested on 26 dogs in 1990. A second-generation ROBODOC® was built by Integrated Surgical Systems, and human trials conducted. In contrast, Kienzle developed a positioning device for total knee replacement (TKR). It locates the tibia and femur, and correctly positions the drill guide for the surgeon. Guide blocks are inserted into the drill holes, allowing the surgeon to accurately prepare the patient's bones for joint implantation. A similar system, named the Acrobot, has been developed by the Imperial College group and is designed for accurate machining of bone surfaces in TKR surgery. All the systems mentioned depend on preoperatively placed fiducial markers. Patents on this development are U.S. Pat. Nos. 5,695,500; 5,397,323 (both Taylor) U.S. Pat. No. 5,086,401 and U.S. Pat. No. 5,408,409 (both Glassman) issued in 1992 to 1997.

Robots designed for neurosurgical applications are generally restricted to positioning and holding instruments for simple procedures such as stereotactic biopsies.

In 1991, Drake reported the use of a PUMA 200 robot as a neurosurgical retractor in the resection of six thalamic astrocytomas. It is the same machine that was first used by Kwoh in 1985 to perform stereotactic biopsies. The robot has revolute joints and has six DOF. Individual joints are moved by DC servomotors, and their position and velocity tracked by optical encoders. The robot arm could be programmed to move into position, or manually manipulated in a passive mode. Its repeatability was measured at 0.05 mm, and error of accuracy at 2 mm. Its pneumatic gripper was used to clasp a brain retractor only. The cases were all performed with a BRW stereotactic frame in place, secured to the same rigid structure as the PUMA arm. This allows for stable transformation of stereotactic to robotic coordinates. Target coordinates were transferred to a computer work station with 3D CT images, enabling the brain retractor to be accurately placed in relation to the lesion. Progress in developing this system was limited by the inability to rapidly render updated 3D brain images in the operating room. The recent convergence of advanced computing, software and iMR imaging now allows us to initiate sophisticated neurorobotics.

A six DOF robot has also been used by Benabid from 1987 to position brain cannulae. It is attached to a stereotactic frame, and can use spatially encoded data from Xray, CT, MR imaging and angiography to plot its path. These images are also fused with digitized brain atlases to assist in surgical planning. Hundreds of stereotactic cases have been performed, including endoscopy (1-3). Similarly, URS (Universal Robotic Systems) has developed a six DOF hexapod robot called Evolution 1 for brain and spinal surgery. This system is based on a parallel actuator configuration, which provides it with high positional accuracy and large payload capacity. The positional accuracy is essential for stereotactic procedures and the high payload capacity may make Evolution 1 particularly well suited for drilling applications such as pedicle screw placements in the spine.

A simulation tool for neurosurgery, ROBO-SIM, has recently been developed. Patient imaging data is entered and the surgical target and corridor can be selected and planned. Virtual constraints are determined, creating no-go zones. The system can be connected to a robotic arm, NEUROBOT, which holds and positions an endoscope for the surgeon. NEUROBOT has four degrees of freedom if pivoted around the burr-hole. At this time, there are no published reports of it being used on patients. It is attached to a stereotactic frame, and can use spatially encoded data from Xray, CT, MR imaging and angiography to plot its path. Again, the systems have only one robotic arm and cannot emulate a human surgeon.

A dextrous robot called the Robot-Assisted Microsurgery system (RAMS), was developed by NASA's Jet Propulsion Laboratory. The mechanical subsystem is a six-DOF robot slave arm driven by tendons. This allows a large work envelope. It is designed to have 10 microns positioning accuracy. The master input device also has six tendon-driven joints. Simulated force feedback has been used, and it has potential to be used tele-robotically. RAMS is capable of being used to enhance various types of microsurgery, including ophthalmology. Although RAMS has the required dexterity, it is still a single arm system lacking the ability to reposition itself over a large worksite. It is also not MR compatible and has no direct force feedback sensing capability and is not image-guided. Patents on this development are U.S. Pat. Nos. 5,784, 542; 5,710,870; 6,385,509 and 6,233,504 all of Das and Ohm et al issued in 1998, 2001 and 2002.

The only MR compatible 'robot' is a simple experimental system developed by Chinzei and at the Brigham and Women's Hospital in Boston, USA. The robot consists of a passive instrument holder attached to Cartesian translational stages. The limited capabilities of the device caused it to fall into disuse.

The progress of clinical neurological sciences has depended on accurate cerebral localization and imaging technology. Over the past century, advances in cerebral imaging including contrast angiography, pneumoencephalography, and in more recent decades, ultrasound imaging, CT, MRI and frameless stereotactic navigation technology have revolutionized cerebral localization. Neurosurgery's dependence on imaging technology is epitomized by the recent flurry of iMR imaging systems developed to provide MR images during a neurosurgical procedure. Since 1996, multiple MR systems and related technologies have been developed, with over 3000 neurosurgical procedures performed worldwide. The systems possess magnet field strengths ranging from 0.12 to 1.5 Tesla, associated with varying degrees of intrusion into standard neurosurgical, anaesthetic and nursing procedures and protocols.

SUMMARY OF THE INVENTION

According to one aspect of the invention there is a provided an apparatus for use in surgical procedures comprising:
- a robot for operating on a part of a patient, the robot including:
- a movable support assembly arranged to be located in fixed position adjacent a patient;
- two movable arms each carried on the support assembly;
- each arm having redundant degrees of freedom of movement;
- each arm having an end effector for carrying various surgical tools (one at a time) for operation on the patient;
- each end effector including force sensors for detecting forces applied to the tool by engagement with the part of the patient;
- a microscope arranged to be located at a position for viewing the part of the patient;
- and a workstation and control system including:
- a pair of hand-controllers, simultaneously manipulated by a single surgeon, each operable to control movement of a respective one of the arms;
- each hand-controller having force feedback arranged to be controlled in response to the detected forces for providing haptic feedback to the operator;
- a first display for displaying at least one image from the microscope; and
- a second display for displaying on an image of the part of the patient the real-time location of the tool.

The device described in more detail hereinafter is a surgeon-operated robotic system for neurosurgery that is compatible with a Magnetic Resonance (MR) imaging system. The system allows a microsurgeon to manipulate tools tele-robotically from a control room adjacent to the operating theatre, or at a considerable distance (e.g. intercontinental and low earth orbit), and works with a specialized set of modified tools based on a subset of the standard neurosurgical tool set. The robot and tools provide 16 degrees-of freedom (DOF) movement and consists of two independently controlled surgical arms (each with eight DOF) and a camera system to view the work-site. Its function is integrated with a microscope which is placed behind the robot base, except when the robot is in stereotaxy mode and has moved down the bore of the MRI system.

The arrangement described provides a safe surgical robot that:
- has two robotic manipulators to perform surgical functions with a precision and dexterity better than the best neurosurgeon;
- is compact enough to fit and work inside an MRI magnet bore;
- is completely non-magnetic including all mechanical structures and actuators and does not interfere with MR imaging;
- allows a variety of neurosurgical tools to be used;
- achieves true image-guided surgery by registration of iMRI fiducials registered by a digitizer on the robot base, and updating this positional data with information from encoders in the robot joints. This enhances the surgeon's situational awareness by constantly updating the position of the tool tips in relation to the surgical target; and
- provides the surgeon with a sense of feel in three DOF, that is it has haptic capability.

The robotic system has two basic modes of operation: microsurgery, and stereotactic surgery. Cranial stereotactic procedures will take place within the bore of the magnet. Microsurgical procedures will be performed outside the magnet and will involve other staff working co-operatively with the robotic system.

The use of robotics in microsurgery allows for precise motions that can be guided by microscope and/or MR images obtained during the surgical procedure, and represents a significant advance in this field. The robot will be used for parts of the procedure that require precise, tremor free motions or geometric accuracy, and as a link between the MR images and physical reality.

The system consists of a Neurosurgical Robot, a System Controller and a Surgical Workstation. The physician controls the neurosurgical robot, located in the Operating Room, via a Surgical Workstation located in a separate Control Room. FIG. 1A is a schematic view of the use of this system with an MRI machine. The system architecture is based on a "master-slave" control where the robot arm motions are slaved to the hand-controllers manipulated by the surgeon. To enhance smooth and precise motion of the surgical tool, tremor filters are incorporated and the motions of the arm may also be scaled down.

The workstation consists of the Human-Machine Interface (HMI), computer processors, and recording devices. The HMI includes two hand controllers that are used to control the spatial position and actuation of the surgical tools grasped by each arm. The surgical workstation is equipped with 4 display panels and one binocular display: one showing the 3D MR image of the brain and a real-time position of the surgical tool within the operating site; a computer status display showing system data of the robotic system; a real-time color view of the operative site captured by a field of view camera system; a 2D high resolution display of the operative field, and a 3D binocular display of the operative field. Both of the microscope displays are interfaced with high resolution cameras mounted on the right and left ocular channels of a standard surgical microscope. An additional display provides system data and control settings. The workstation contains recording devices to store intra-operative MRI and video imagery and system data. An electrical cable harness connects the robot to the System Controller. The controller translates the workstation and hand-controller commands into inputs for the robotic arm motor drives and sensors. The System Controller contains the servo-control electronics that independently move and position the robot arms. The System Controller also includes an interface for the optical joint encoders and thermistors. The backbone of the System Controller is an elaborate array of software modules and electrical hardware. The architecture of the System Controller is designed to enhance safety by single fault tolerant software and redundant electrical back-up.

The robot consists of two articulated arms with dexterous mechanical manipulators that grasp and move surgical tools attached to the arm end-effectors.

For precise tool positioning, each of the surgical arms has eight DOF. The arms are each independently small enough to operate within the confines of the working diameter of the IMRIS closed bore magnet and the device can be operated to select one or the other arm. Both can work simultaneously within an open magnet of either vertical or horizontal design. They provide frame-less stereotactic functionality when registered to fiducial markers on the head or spine. Such fiducial markers may comprise a component which can be mounted on the patient and define artifacts which can be viewed in the MR image. Such MR viewable objects are usually spherical and are made from an MR responsive material which thus generates a readily visible artifact on the MR image. Other types of optical and MR responsive objects can be used. These targets are localized and registered using a robot base-mounted mechanical digitizing arm. The images defined by the MR system can be registered relative to the arms of the robot allowing the surgeon to place the tools at the required location as determined by the MR analysis.

The robot is mounted on a vertically adjustable mobile base, moved into position for the surgical procedure, and mechanically secured using locking wheels. The robot can be positioned to function as an assistant or the primary surgeon. The mobile base enables the robot to be integrated into any operative environment equipped with the appropriate electronic and mechanical interfaces.

Surgical tools are manually inserted into the arm end-effectors. The location and orientation of the tool tip relative to the surgical target will have an accuracy of approximately one-millimeter when relying on frameless navigation alone. Further refinement of toll tip placement is based on the surgeon assessing the stereoscopic, magnified field of view provided by the binoculars at the workstation. The final accuracy achieved is therefore only limited by the combination of the spatial resolution of our visual system (rods and cones) with 30 micron resolution that our robot has achieved on breadboard testing. The location of the tool tip can be continuously monitored using the internal arm joint angles and the virtual display of the tool acquired from iMRI.

The robot and field camera are designed to be compatible with the MR environment. Compatibility ensures that the robot produces minimal MRI artifact and conversely, the operation of the robot is not disturbed by the strong electromagnetic fields generated by the MR system. All equipment exposed to the MR field uses compatible materials, components and design practices such as:

The robot drive mechanisms use an Ultrasonic piezo-electric actuator technology.

The arms and surgical tools are made of MR-compatible materials.

All electronics are RF and magnetically shielded.

Optical force sensors/strain gauges are attached to the tool interfaces to provide force-feedback inputs. The sensors are MR compatible, immune to electromagnetic interference and possess high sensitivity and fast measurement update rates.

The workstation controls the arms by transforming commands from the hand controllers and transmitting them to the Main Controller. The hand controllers act as virtual tools for the surgeon. The motion commands are filtered to remove hand tremor and typically scaled down so, for example, a 10 cm displacement of the controller would result in a tool tip displacement of 5 mm. As a safety measure, the arms are only activated if a hand switch is depressed. This will avoid inadvertent movement of the arms caused by an accidental bumping of the hand controller. In addition to providing commands to the robot, the workstation receives feedback from the robot, the Main Controller, the MR system and other devices.

The workstation has three display types: Video, MRI and Control. The video recordings of the surgical worksite are taken by stereo cameras mounted on the surgical microscope and displayed on a high resolution 2D display and a 3D binocular display, providing the surgeon with a sense of depth. A third video display is used to show a video image of the operating room. The MRI display shows the patient's imaging data with a virtual tool position superimposed on the image. This enables the surgeon to view and track the tool in real-time, thereby facilitating image-guided surgery. The MRI can be enhanced by the administration of intravenous contrast agents to show the lesion and its relationship to adjacent structures. Lastly, the Control display is used to monitor the control systems of the robot.

Surgical simulation software on the workstation allows the surgeon to plan the point of cranial trepanation and calculate safe trajectories for the surgical corridor. Virtual 'no-go' boundaries can be defined by the surgeon, preventing inadvertent injury to neural elements. The procedure can be practiced in virtual mode by the surgeon. This will be particularly useful when performing a rare procedure, as well as in helping to teach trainee neurosurgeons.

The following sections outline the systems, electromechanical, and workstation components and specifications.

System Description

The workstation consists of the crucial Human-Machine Interface (HMI), computer processors, and recording devices. The HMI includes two hand-controllers used to control the motion and position of the surgical tools grasped by each arm. The surgeon has multiple surgical displays: one showing the 3D MR image of the brain and a real-time position of the surgical tool within the operating site, and the other a real-time color view of the surgical site captured by the surgical microscope. A third display will provide system data and control settings. The workstation contains recording devices to store intra-operative video imagery and system data. An electrical cable harness connects the robot to the Main Controller. The controller translates the workstation and hand-controller commands into inputs for the robotic arm motor drives. The Main Controller contains the servo-control electronics that independently move and position the robot arms. The Main Controller also includes an interface for the optical joint encoders and thermistors. The backbone of the Main Controller is an elaborate array of software modules and electrical hardware. The architecture of the Main Controller is designed to enhance safety by single fault tolerant software and redundant electrical back-up.

Electro-Mechanical Components

The robot is configured as a yaw plane manipulator to reduce the number of joints affected by gravity. It consists of two articulated arms with dexterous mechanical manipulators that grasp and move surgical tools attached to the arm end-effectors. A vision system consisting of an MR compatible camera system and white LED lights is mounted on the base and manually adjusted.

For precise tool positioning, the surgical arms have 8-DOF per arm (including tool actuation). The arms are small enough to individually operate within the confines of the 68-cm working diameter of the 1.5 T magnet. The robot is mounted on a mobile base, moved into position for the surgical procedure, and mechanically secured using wheel brakes. The robot can be positioned to function as an assistant or the primary surgeon. The mobile base enables the robot to be integrated into any operative environment equipped with the appropriate electronic and mechanical interfaces.

Surgical tools are manually inserted in the arm end-effectors. For microsurgical procedures, standard tools such as forceps, needle drivers, suction, micro-scissors and dissectors are created to fit the end-effectors. The tool actuation mechanism is comprised of a mobile ring surrounding the tool handle, the vertical movement of which controls tool actuation. Circular movement of a gear mechanism generates tool rotation. Based on the end-effector configuration, a novel micro-scissor design was implemented. For stereotactic procedures, a linear drive mechanism was designed to provide accurate insertion and targeting of a cannula and introducer. Each tool is equipped with an identifier bar and color code to automatically configure software 3D models. The models are used to calculate the location and orientation of the tool tip relative to the surgical target to an accuracy of one-millimeter. This absolute accuracy is limited by the resolution of inputs from the spatially encoded MR data and also the registration method. The registration method involves calibrating the robot coordinate frame to the MR image of the patient using MR fiducials and mechanical digitizing points. The location of the tool tip is continuously monitored using a kinematic model combined with internal arm-joint angles and the virtual display of the tool acquired from iMRI or other imaging modalities such as 3D ultrasound. The tool position is calibrated mechanically and checked against its position determined from updated MR images. An incremental tool tip resolution of 30 microns can be obtained.

The robot and field of view camera are designed to be compatible with the MR environment. Compatibility ensures the robot produces minimal MRI artifact and conversely, the operation of the robot is not disturbed by the strong electromagnetic fields generated by the MR system. All equipment exposed to the MR field utilizes compatible materials and components including:

Piezoelectric motors are used for the robot drive mechanisms. They have the advantage of being non-magnetic, self-braking, MR-compatible, and able to meet the operating time specifications.

Material selection is critical for robot stiffness and MR compatibility. The upper and lower arm structural components are made of titanium and PEEK (Polyetheretherketone) respectively. Both materials have a very high resistivity, permitting placement inside the RF coil during transmission with minimal degradation of the coil quality factor. The intra-operative magnet and RF coil can accommodate titanium and PEEK in the imaging volume without significant loss of performance.

All electronics are RF and magnetically shielded and located as far from the high intensity fields as practical.

A three DOF optical force sensor system is used to provide haptic feedback to the surgeon. The design is based on the photo-elastic effect to measure strains in materials under stress. The end-effector is equipped with deformable flexures providing an interface for the surgical tools. Each flexure is positioned mutually perpendicular and contains its own optical strain sensor. This arrangement allows strains to be measured at the flexure surfaces. These strain measurements are used to calculate tool tip forces in the X, Y, Z directions, which are then sent back to the workstation hand controllers.

Surgical Workstation

The Surgical Workstation incorporates a computer processor, two hand-controllers to manipulate the robot arms, a controller for positioning the microscope and lights, three types of display, and data recorders. The interface is designed to maximize ergonomic comfort and minimize surgeon fatigue.

In addition to providing commands to the robot, the workstation receives feedback from the robot, the Main Controller, the MR system, and other devices. The type of information received includes: Video from the stereo camera viewing the surgical work site via the microscope; preoperative and iMR image data; tool position and motion data from the robot controller; force-sensing (haptic) data from each arm; diagnostic or error messages from the robot controller; simultaneous talk/listen voice communication with operative staff; and patient physiologic data.

Hand-Controllers

The workstation controls the arms by transforming commands from the hand-controllers and transmitting them to the Main Controller. The hand-controllers act as virtual tools for the surgeon and have 6-Degrees-of-Freedom (DOF) with 3-DOF positional force feedback. The system has a large workspace and high force feedback fidelity. Motion commands are filtered to remove hand tremor and typically scaled down. For example, a 10-cm displacement of the controller could result in a tool tip displacement of 5 mm. As a safety measure, the arms are only activated if a hand switch is depressed. This avoids inadvertent movement of the arms caused by an accidental bumping of the hand-controller. The user interface of the hand-controller has been designed to maximize ergonomic comfort.

Visual Displays/Optics

The Video display presents a 3D stereoscopic view of the surgical site providing the surgeon with a sense of depth. Two precision aligned video cameras are fitted to the right and left ocular channels of a standard surgical microscope. Camera signals are presented on a proprietary high-resolution virtual stereomicroscope (binoculars) at the workstation. The same camera signal is displayed on a 2D—HDTV (High Definition Television) screen. The HDTV is positioned above the binoculars and serves as an alternative visual display for the surgeon and as a primary display for surgical staff and students. The binocular display was chosen over conventional 3D stereoscopic displays with polarization glasses to minimize the effects of ghosting and also to increase contrast and color depth of the image. The microscope is equipped with a support stand capable of motorized tilt of the microscope head. These mechanized features of the microscope allow the surgeon to remotely adjust the microscope head from the Surgical Workstation. Magnification and working distance can be controlled from the Workstation.

The MRI display shows a virtual tool position superimposed on the images. This enables the surgeon to view and track the tool in real-time, thereby facilitating image-guided surgery. The MRI is enhanced to show the lesion and its relationship to adjacent structures in both 2- and 3-dimensions.

The Control Panel display will show the following data:
System configuration: operational modes, calibration, hand-controller parameters
Robot status: tool angles and depth, system status messages, force sensor data
Physiological data: heart rate, blood pressure, expired pCO2, urinary output, blood loss, oxygen saturation
Operational scripts to outline the step-by-step procedures and contingencies Image Guidance, Simulation, and Registration The image guidance system of robot provides the surgeon a means of navigation, target localization and collision avoidance. Surgical simulation software on the workstation allows the surgeon to plan the point of cranial trepanation and calculate safe trajectories for the surgical corridor. Virtual boundaries defined by the surgeon prevent inadvertent injury to neural elements. Simulated procedures can be practiced in virtual mode by the surgeon.

Registration of the robot is performed using a pre-operative MRI scan and MR fiducial targets that remain near the surgical field throughout the operation. The registration between the robot and the fiducials is accomplished using a compact 3-D digital coordinate measurement arm (digitizer) located on the base of the robot. The surgical assistant uses the digitizer arm to measure the coordinates of touch points on registration targets located near the surgical field. The coordinates are transmitted to the workstation, which uses the data to calculate the geometric coordinate transformation.

Safety Challenges and Solutions

It is a purely passive device and is exclusively controlled by an experienced surgeon at the workstation. An additional surgeon will also be scrubbed for microsurgical cases and will be able to manually intervene if ever needed. Audio communication between the robot operator and the OR team will be provided, and a video display of the worksite and MRI display duplicated in the OR. The robot's work envelope is tailored to a specific procedure, and suitably restricted. In addition to this, no-go zones are programmed into the proposed operation during the surgical planning phase. The software controlling the robot insists on continuous input from the surgeon, and a dead-man switch (safety interlock) also requires ongoing activation to prevent a lockdown. A user selectable limit is set via the software that will limit the amount of force that can be applied and can be affected by a current limit set at the servo level. If actuators fail, intrinsic braking will automatically freeze the robot. The actuators themselves are designed to function at low torque and force levels, reducing the risk of tissue injury. This has the added benefit of using small, light motors that enhance robot balance and dexterity. End-effector/tool motion will also be considerably slowed down when operating within a microsurgical corridor. It can perform dissection at a pace of 1 mm/sec or be accelerated to as much as 200 mm/sec when outside the work envelope and reaching out for tool changes. The transition to faster speeds will require two sequential but different electronic commands to prevent accidental speeding. The mobile iMRI also has inbuilt braking systems and moves at slow speeds as it approaches patients. Unplanned power interruption results in 'default' freezing of movements, and personnel can deliberately cut power through strategically placed emergency stop (E-Stop) buttons.

Clinical curbs also minimize patient risk. The current robot is excluded from performing skull exposure, as this would be a relatively difficult task for a robot but is efficiently accomplished by a surgeon. Similarly, burr-holes and bone-flaps are executed by surgeons.

The system provides an MR-compatible ambidextrous robotic system capable of microsurgery and stereotaxy. With additional surgical toolsets this system lends itself to other disciplines including plastic, ophthalmological and ENT surgery. The system has a uni-dexterous configuration for deployment within a magnet bore allowing updated image guidance for stereotactic procedures. This configuration provides additional range of motion within the magnet bore. Complex microsurgery, where both robotic arms are employed, is performed outside the magnet under supervision of a scrubbed surgeon. This will also facilitate safety and tool changing.

The system has been created de novo for the specific purpose of performing microsurgery and stereotaxy. This includes standard techniques such as micro-dissection, thermo-coagulation, and fine suturing. Procedures such as tumor resection and aneurysm clipping are possible. The design of the robot is inclusive and versatile however, and is ideal in other microsurgical specialties such as ophthalmology. The fine dexterity and low payload of the end-effectors precludes their use in gross manipulation of tissue and bone, as these tasks are more readily suited to humans. Other unique features include MRI-compatibility as tested at 3 T, and a mechanical navigation system. This makes the system the first truly image-guided surgical robot. It is also the only surgical robot with eight-DOF per arm (including tool actuation). Although this is significantly less than human DOF, it exceeds the six-DOF required to position a tool precisely in space and then orient it in the desired plane. Unnecessary DOF result in cumulative instability while insufficient DOF result in limited positioning of the manipulator. Surgeons performing microsurgery will instinctively eliminate redundant DOF by fixing their shoulder and elbow joints, but retain adequate dexterity in the hands and wrists to perform delicate microsurgery. The manipulators were designed to have the necessary dexterity to perform these same tasks.

The system provides the first authentic force feedback system in surgery. Coupled with an exceptional visual system, based on military optics, and auditory feedback from the surgical site, the system recreates the sound, sight and feel of conventional neurosurgery. The haptic sensibility component will also be useful for simulating rare procedures, and teaching neurosurgical residents.

BRIEF DESCRIPTION OF THE DRAWINGS

One embodiment of the invention will be described in conjunction with the accompanying drawings in which.

DETAILED DESCRIPTION

Further details of the above generally described system are shown in the attached drawings 1 through 17.

Figure 1A:
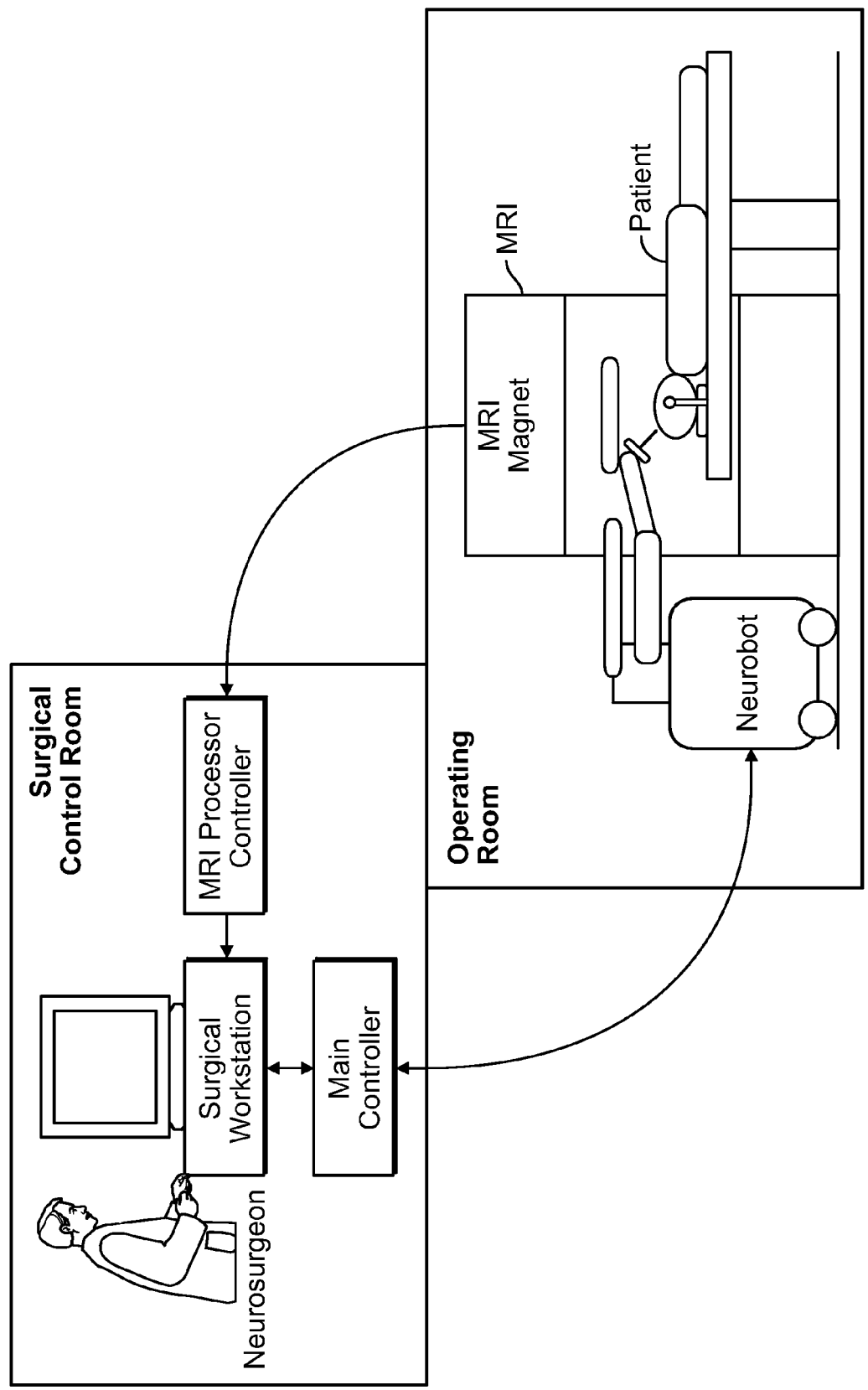
FIG. 1A is a schematic view of a neurosurgeon, surgical workstation, main controller, and MRI processor and controller located in a surgical control room while the robot (labeled "Neurobot" in the figure), the MRI magnet and the patient are located in an operating room.
Figure 1B:
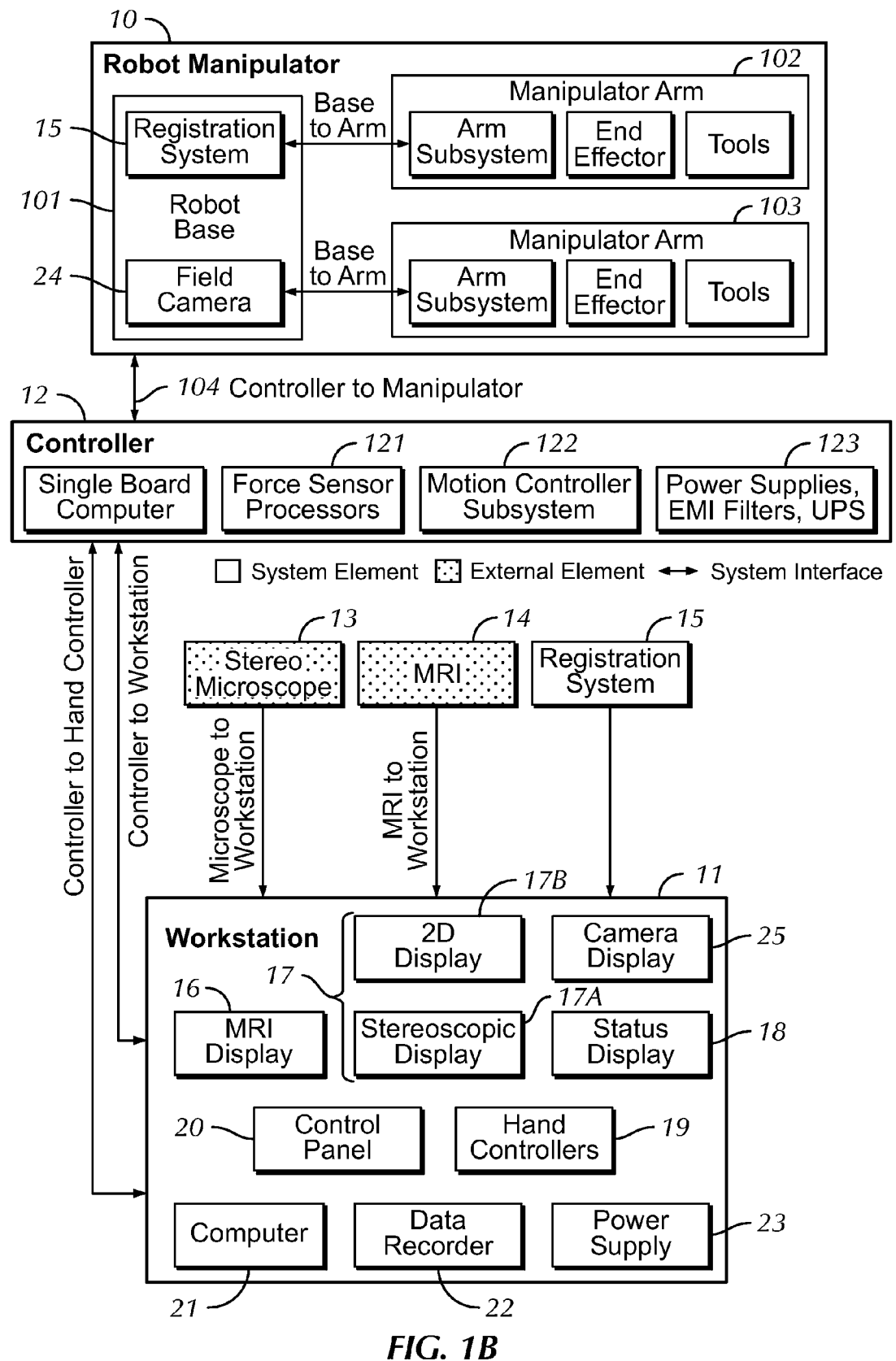
FIG. 1B is a schematic overview of the system according to the present invention.

An overview of the system is shown in FIG. 1B which comprises a robot manipulator 10, a work station 11 and a controller 12 which communicates between the robot manipulator and the work station. As inputs to the work station is also provided a stereo microscope 13, an MRI imaging system 14 and a registration system 15.

The work station includes a number of displays including at first display 16 for the MRI image, a second display 17 for the microscope image and a third display 18 for the system status. Further the work station includes two hand controllers schematically indicated at 19 and an input interface 20 allowing the surgeon to control the systems from the work station while reviewing the displays. The work station further includes a computer or processor 21, a data recording system 22 and a power supply 23.

The display 17 includes a stereoscopic display 17A which provides a simulated microscope for viewing the images generated by the stereo-microscope system 13. Further the display 17 includes a monitor 17B which displays a two dimensional screen image from the microscope system 13.

The robot manipulator 10 includes a field camera 24 which provides an image on a monitor 25 at the work station.

Figure 4:
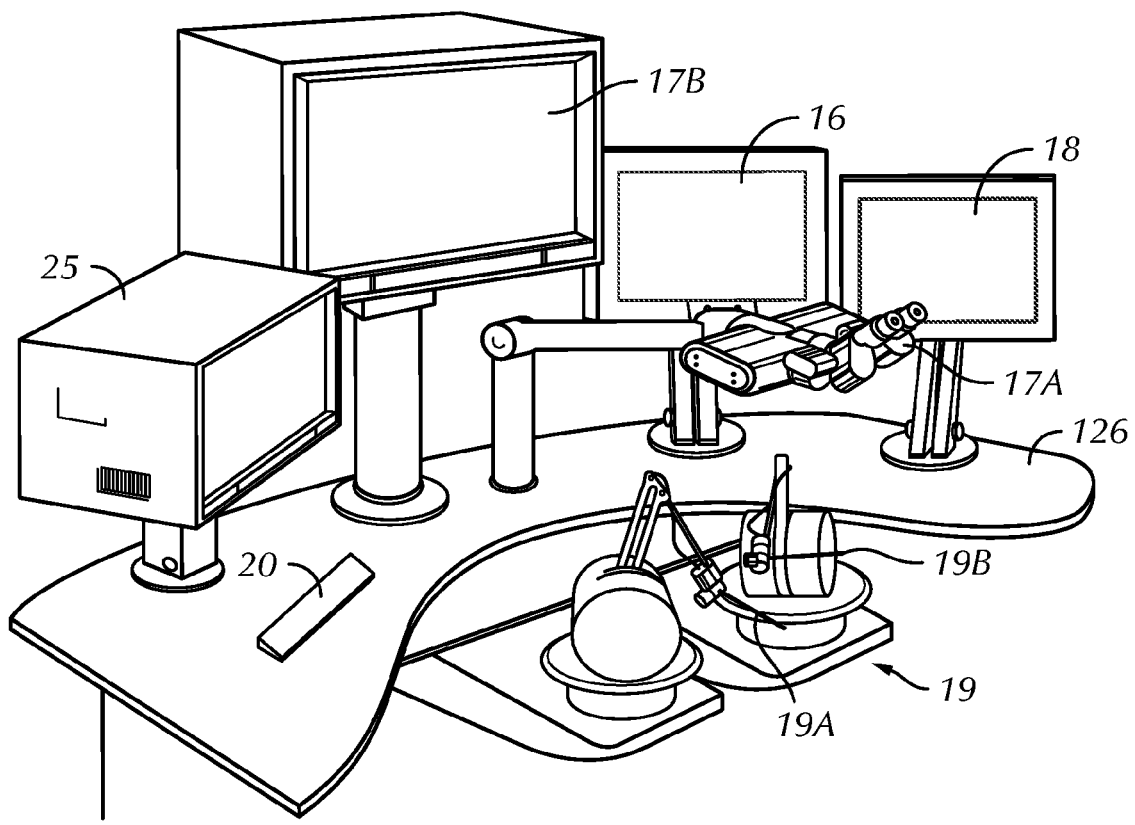
FIG. 4 is an isometric view of the workstation of the system of FIG. 1B.

Turning to FIG. 4, a typical layout of the work station is illustrated which comprises a desk 126 on which is mounted four monitor screens 16, 17B, 18 and 25 together with a microscope viewing system 17A, all of which are arranged to be accessed by the surgeon seated at the desk. In front of the desk is provided the hand controllers 19 and the input terminal 20.

The stereo microscope system is of a type which is commercially available and can be mounted on a suitable support adjacent the patient for viewing the necessary site. The stereo microscope includes two separate imaging systems one for each channel which are transmitted through suitable connection to the display 17 at the work station. Thus the surgeon can view through the microscope display 17A the three dimensional image in the form of a conventional microscope and can in addition see a two dimensional image displayed on the monitor 17B.

Similarly the magnetic resonance imaging system 14 is of a conventional construction and systems are available from a number of manufacturers. The systems are of course highly complicated and include their own control systems which are not part of the present invention so that the present workstation requires only the display of the image on the monitor 16 where that image is correlated to the position of the tool as described hereinafter.

The hand controllers 19 are also of a commercially available construction available from a number of different sources and comprise 6 degrees of freedom movable arms which can be carefully manipulated by the surgeon including end shafts 19A which can be rotated by the surgeon to simulate the rotation of the tool as described hereinafter. An actuator switch 19B on the tool allows the surgeon to operate the actuation of the tool on the robot as described hereinafter.

Figure 2:
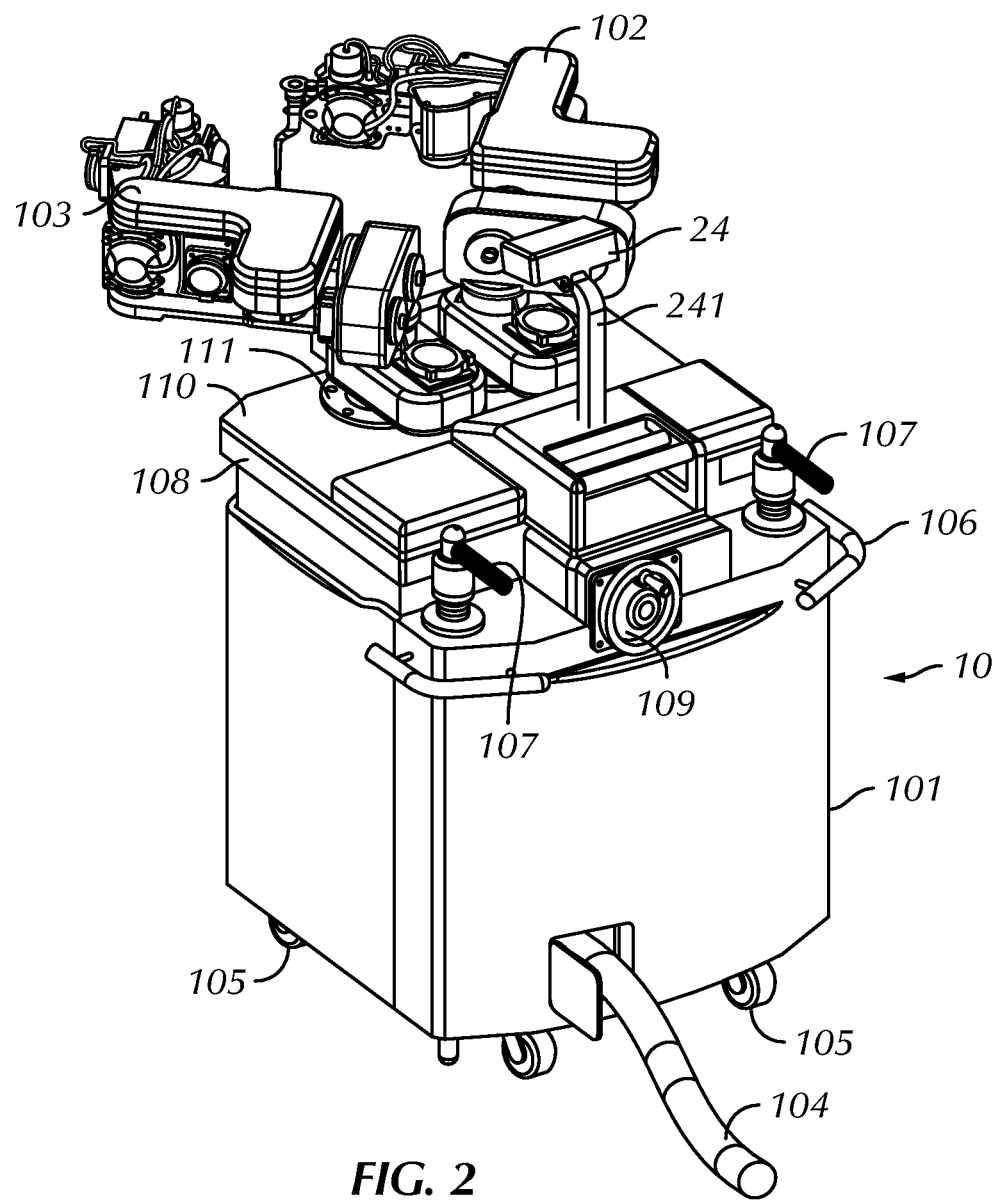
FIG. 2 is an isometric view from the rear and one side of the robot of the system according to the present invention.
Figure 3:
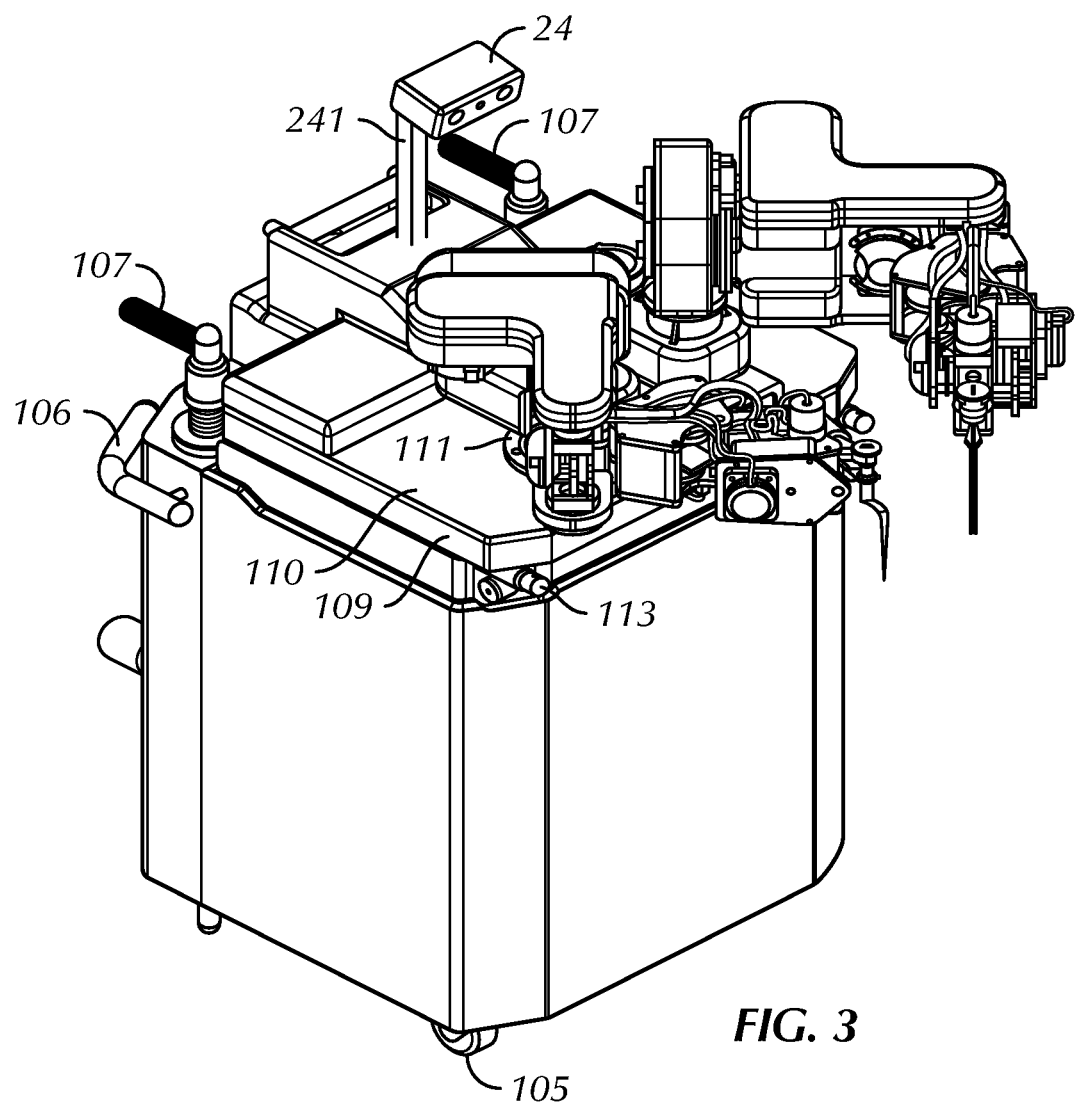
FIG. 3 is an isometric view of the robot of FIG. 2 from the front and opposite side.

The robot manipulator shown in general in FIG. 1B and shown in more detail in FIGS. 2 and 3 comprises a cabinet 101 and two arms 102 and 103 which are mounted on the cabinet together with the field camera 24 which is also located on the cabinet. The field camera is mounted at the back of the cabinet viewing past the arms of the front of the cabinet toward the patient and the site of operation to give a general overview field of the situation for viewing on the display 25.

In FIG. 1B is also shown schematically the control system for communication between the work station and the robot manipulator and for controlling the operation of each of those components. The controller includes a force sensor sub system 121 and a motion control sub system 122 together with power supplies and further components as indicated schematically at 123. The force sensor sub system controls the feed back forces as detected at the end effector of the robot arm and describes in more detail hereinafter to the hand control systems 19. The motion control subsystem 122 converts the motion control sensors from the hand-control system 19 into individual operating instructions to the various components of the arms as described in more detail hereinafter. The motion control sub system also provides an output which is communicated to the work station for display on the MRI imaging monitor 16 of the location of the tip of the tool relative to the image displayed on the screen 16, as generated by the registration system 15 as described hereinafter.

As shown in FIGS. 2 and 3, the cabinet 101 includes a communications cable 104 which connects to the controller 12. The cabinet is a mobile unit mounted on castor wheels 105 which allow the cabinet to be moved by handles 106 manually to a required location. Handles 107 act as brakes which lock the wheel and castor rotation so as to locate the cabinet 101 at a required position and maintain it fixed. The cabinet contains suitable ballast so that it is sufficiently heavy to prevent any tilting or toppling or other unintentional movements when the brakes are locked by the handles 107. The cabinet further includes a top section 108 which can be raised and lowered by a manually operable handle 109 so as to raise and lower a top mounting surface 110 which supports base plates 111 of the arms 102 and 103. Thus an operator can wheel the cabinet to the required location and can raise and lower the arms to a pre selected height so as to register with a required location for the site of the operation whether that be microsurgery on an operating table or stereotactic procedures within the bore of a magnet. The field camera 24 is mounted on a stanchion 241 so as to stand upwardly from the top portion 110 and to view forwardly across the arms 102 and 103 to the patient and the site.

Figure 5:
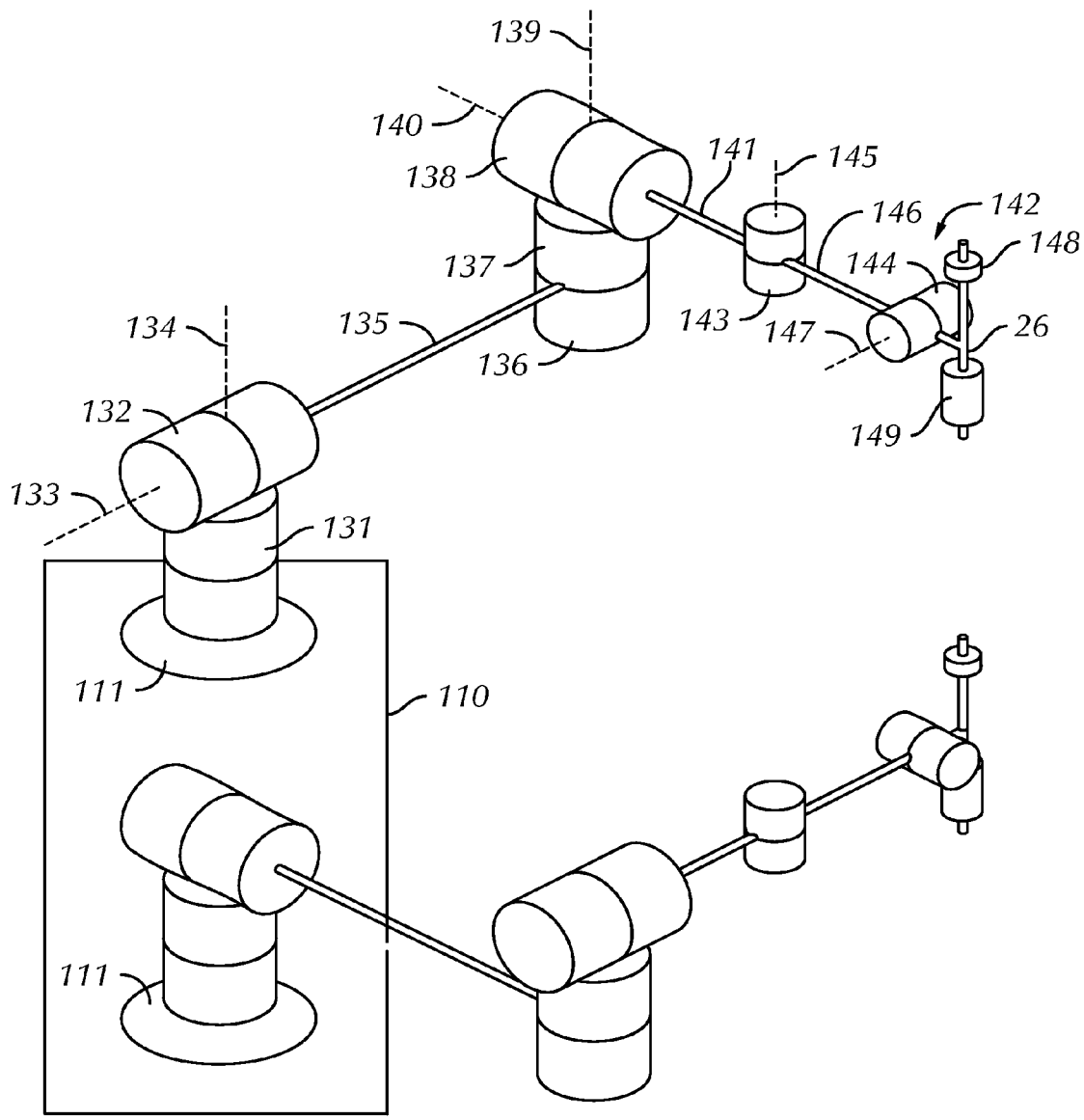
FIG. 5 is a schematic illustration of the operation of the pivots of the arms of the robot of FIG. 2.

For convenience of illustration, the structure of the arms is shown schematically in FIG. 5, where the arms are mounted with their base 111 attached to the top surface 110 and shown schematically. Each of the arms 102 and 103 includes a number of joints as shown and described hereinafter which allow operation of a tool schematically indicated at 26. Thus each arm includes a first joint defining a shoulder yaw pivot 131 defining a vertical axis of rotation. On the vertical axis is mounted a second joint 132 forming a shoulder roll joint which provides rotation around a horizontal axis 133. The shoulder yaw axis 134 extends through the joint 132. A rigid link 135 extends from the joint 132 to an elbow joint 136 which is cantilevered from the shoulder roll joint 132. The elbow joint includes an elbow yaw joint 137 and an elbow roll joint 138. The yaw joint 137 is connected to the outer end of the link 135 and provides rotation about a vertical axis 139. The roll joint 138 is located on the axis 139 and provides a horizontal axis 140. A link 141 lies on the horizontal axis 140 and extends outwardly from the joint 138 to a wrist joint generally indicated at 142. The wrist joint 142 includes a wrist yaw joint 143 and wrist roll joint 144. The wrist yaw joint 143 is located at the outer end of the link 141 and lies on the axis 140. The wrist yaw joint provides a vertical axis 145 about which a link 146 can pivot which carries the roll joint 144. The roll joint 144 provides a horizontal axis 147 which allows the tool 26 to rotate around that horizontal axis 147. The tool 26 includes a roll joint 148 which provides rotation of the tool 26 around its longitudinal axis. The tool further includes a tool actuator 149 which can move longitudinally along the tool to provide actuation of the tool as described in more detail hereinafter.

It will be noted that the axes 134, 139 and 145 are all vertical so that the weight of the supported components has no effect on the joint and there is no requirement for power input to maintain the position of the supported component to counteract its weight.

With regard to the horizontal joint 147, there is nominally a component of the weight of the tool which is applied to cause rotation around the axis 147. However the tool is located close to the axis 147 so that there is little turning moment around the axis 147 resulting in very little weight is applied onto joint 144. Thus the weight component to be rotated around the axis 147 is minimized thus minimizing the amount of force necessary to counteract the weight.

With regard to the axis 140 and the joint 138, it will be noted that the tool and the links 141 and 146 are arranged so that the center of gravity is approximately on the axis 140 thus ensuring the requirement to counteract the weight of those components since those components provide minimum moment around the axis 140.

With regard to the joint 132 and the axis 133, the weight applied to the joint 132 from the link 135 depends upon the position of the joint 137. Thus if the link 141 is aligned with the link 135 then the center of gravity of the cantilevered components from the joint 132 lie substantially on the axis 133 thus minimizing the moment around the axis 133. However it is necessary of course to operate the system that the joint 137 turn the link 141 around the axis 139 thus providing a cantilever effect to one side of the axis 133. However again this moment around the axis 133 is minimized by the selection of the system so that the arm normally operates with the center gravity of the portion of the arm outboard of the link 135 minimized.

Thus the forces required to provide rotation around the various axes is minimized and the forces required to maintain the position when stationary against gravity is minimized.

This minimization of the forces on the system allows the use of MRI compatible motors to drive rotation of one joint component relative to the other around the respective axes.

The arrangement described above allows the use of piezo-electric motors to drive the joints. Such piezoelectric motors are commercially available and utilize the reciprocation effect generated by a piezoelectric crystal to rotate by a ratchet effect a drive disc which is connected by gear coupling to the components of the joint to effect the necessary relative rotation.

Figure 5A:
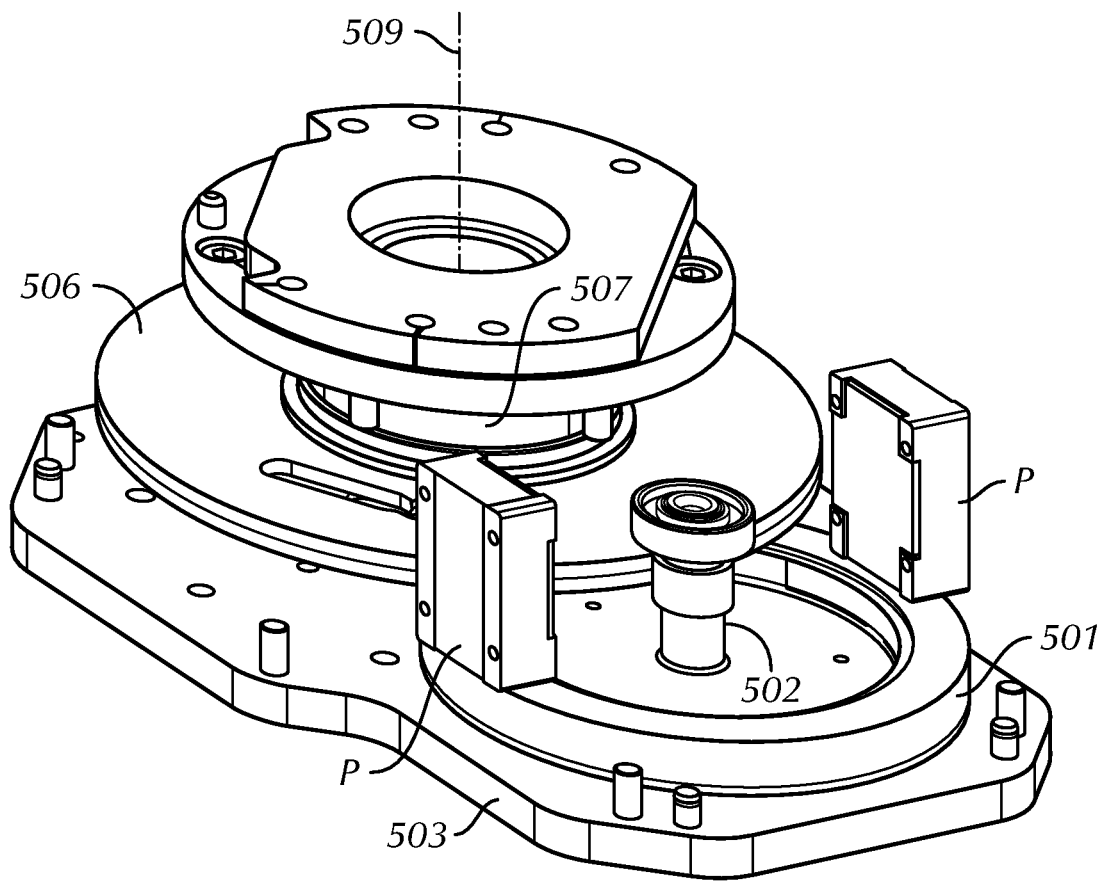
FIG. 5A is a cross-sectional view of one of the pivots of the arms of the robot of FIG. 2.

An open view of a typical joint is shown in FIG. 5A and includes two of the piezoelectric motors P driving a drive plate 501 mounted on a drive shaft 502 carried on the back plate of the housing 503 and in bearings on the front plate (not shown) of the housing. The shaft 502 drives a gear which is in mesh with a driven gear 506 on a driven shaft 507. The driven shaft 507 rotates one part of the joint relative to the other part which is attached to the housing 503 about the joint axis 509.

The joint shown in FIG. 5A uses a dual piezoelectric motor arrangement and is thus used for the larger joints at the shoulder and elbow. For the smaller joints such as the wrist and tool actuation, the same piezoelectric motor is used but one of these motors is used to provide the necessary torque.

Figure 6:
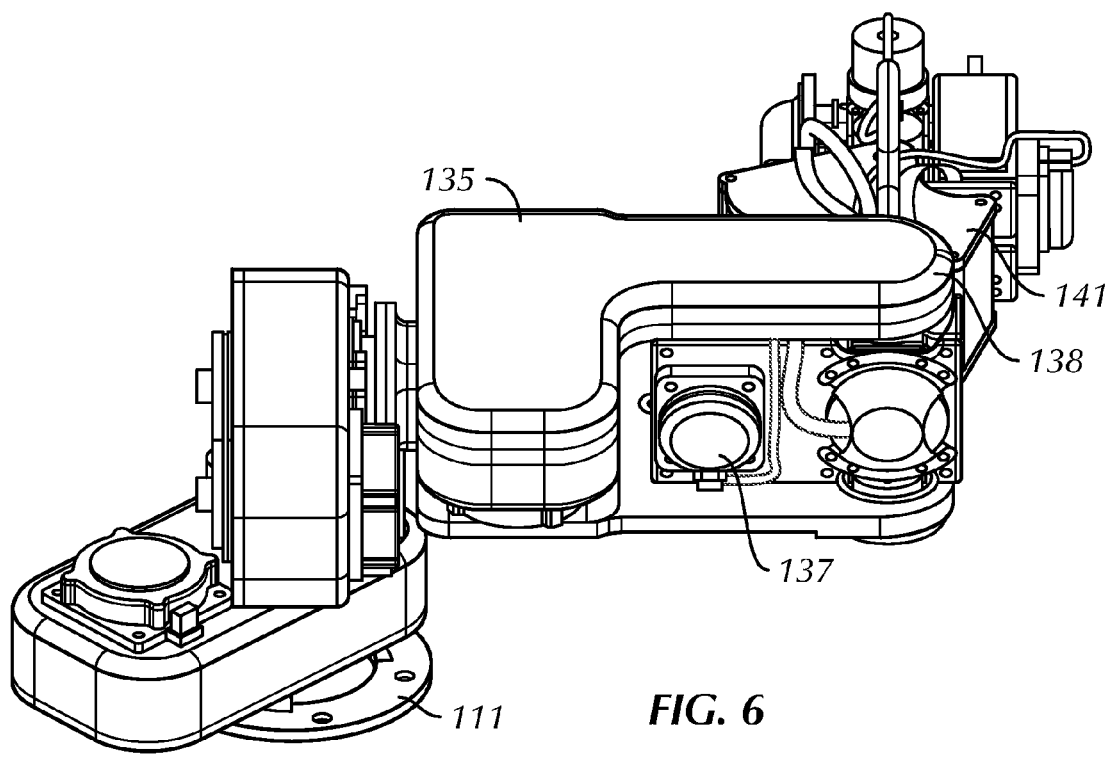
FIGS. 6 and 7 are isometric views of one arm of the robot of FIG. 2.
Figure 7:
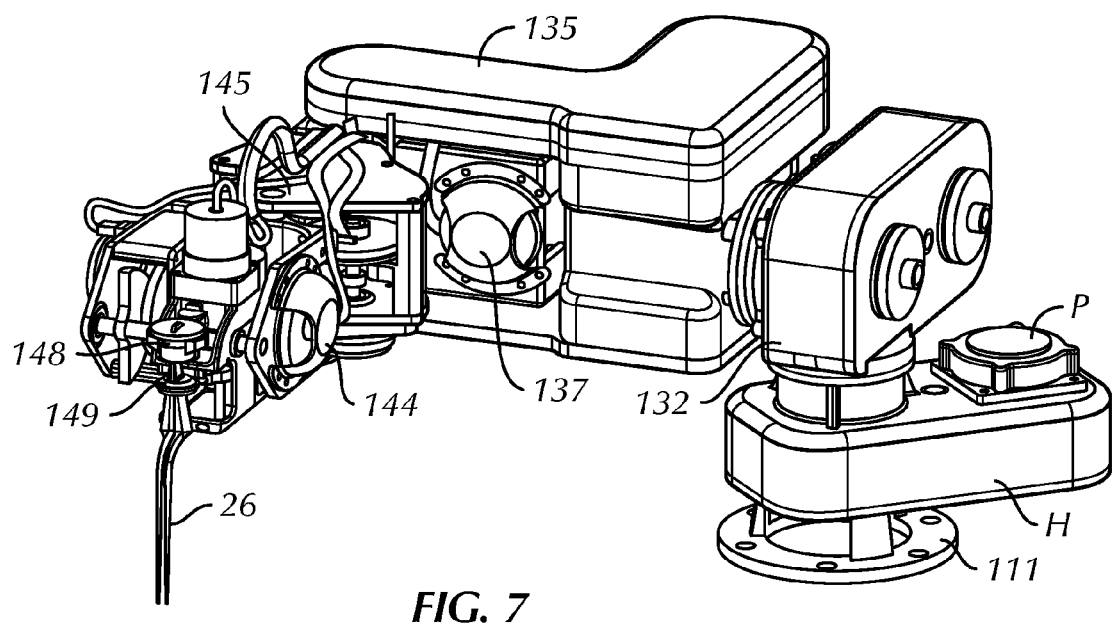

A suitable construction of the motors and links for the arms to embody the schematic arrangements shown in FIG. 5 is shown in FIGS. 6 and 7. Thus the various components are marked with the same reference numerals as set forth in FIG. 5. It will be noted that the joints are of a similar construction with each including a piezoelectric motor P mounted in a housing H. The motor P drives the joint by a gear coupling arrangement from a disc at the motor P to the rotatable portion of the joint on the respective rotation axis. Thus the axis of the motor P is offset to one side of the axis of rotation of the respective joint and provides the required controlled rotation determined by the rotation of the drive disc of the piezoelectric motor. Dual optical encoders shown as 137 are used at each joint to measure joint angle position. The dual arrangement provides redundancy. The encoder is used to determine whether the required movement has been obtained.

Figure 8:
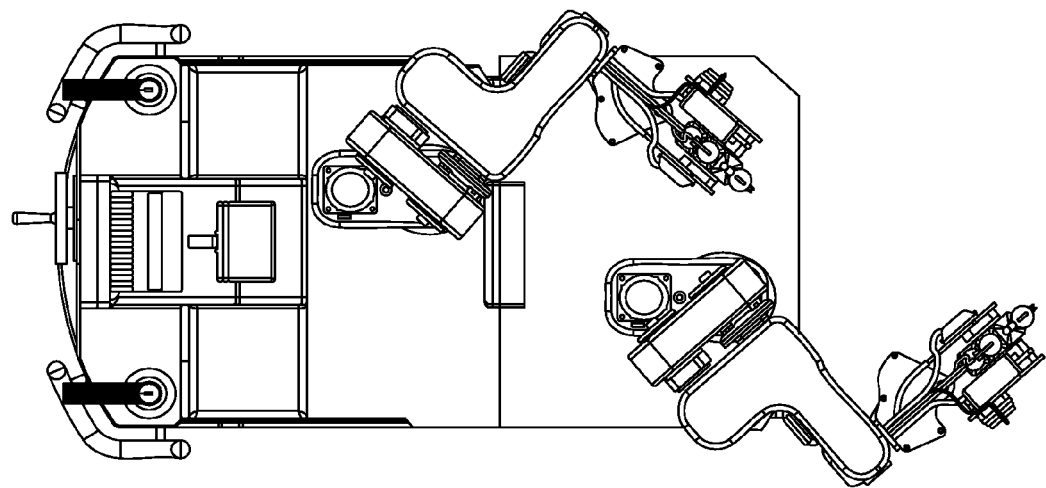
FIG. 8 is a top plan view of the robot of FIG. 1B showing one arm advanced for insertion into a magnet bore of an MRI imaging system and the other arm retracted to allow engagement of the cabinet with the bore.
Figure 9:
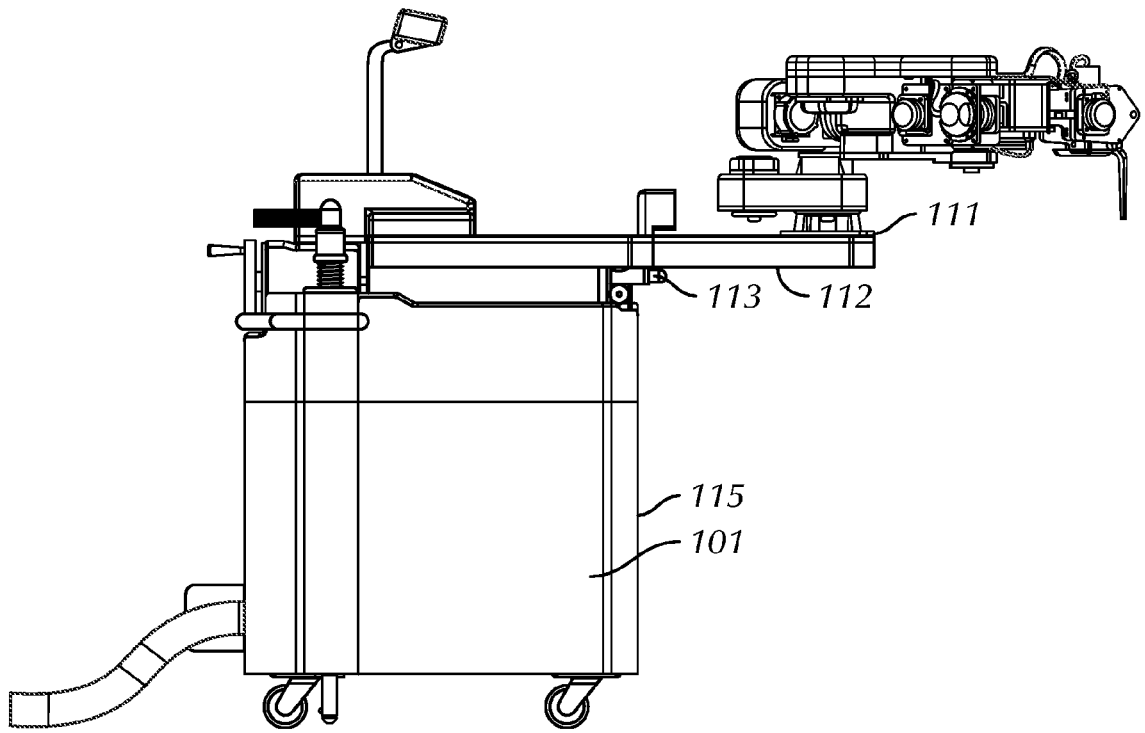
FIG. 9 is a side elevational view of the robot in the configuration of FIG. 8.

Turning now to FIGS. 8 and 9, it will be noted that the construction has been operated to move the arms from the double arm operating system to a single arm operating system for use in co-operation with the bore of a closed bore magnet. Thus in FIGS. 8 and 9, an additional table portion 112 is mounted on the front of the cabinet 101 on mounting pins 113. This allows a selected one of the arms 102 and 103 to be moved with its base plate 111 sliding along a track on the table top 112 to a position advanced in front of a front wall 115 of the base cabinet 101. At the same time the other of the arms is turned to a retracted position so that it is wholly behind the front wall 115 as best shown in FIG. 8. Either of the arms can be selected for movement in a respective track to the forward position since the arms have different work envelopes within which they can move so that, depending upon the location of the site in which operation is to take place, one or other of the arms provides a better field of operation and thus should be selected. The remaining arm remains in place on the table top 110 and is suitable retracted to avoid interference with the opening of the magnet bore.

Figure 10A:
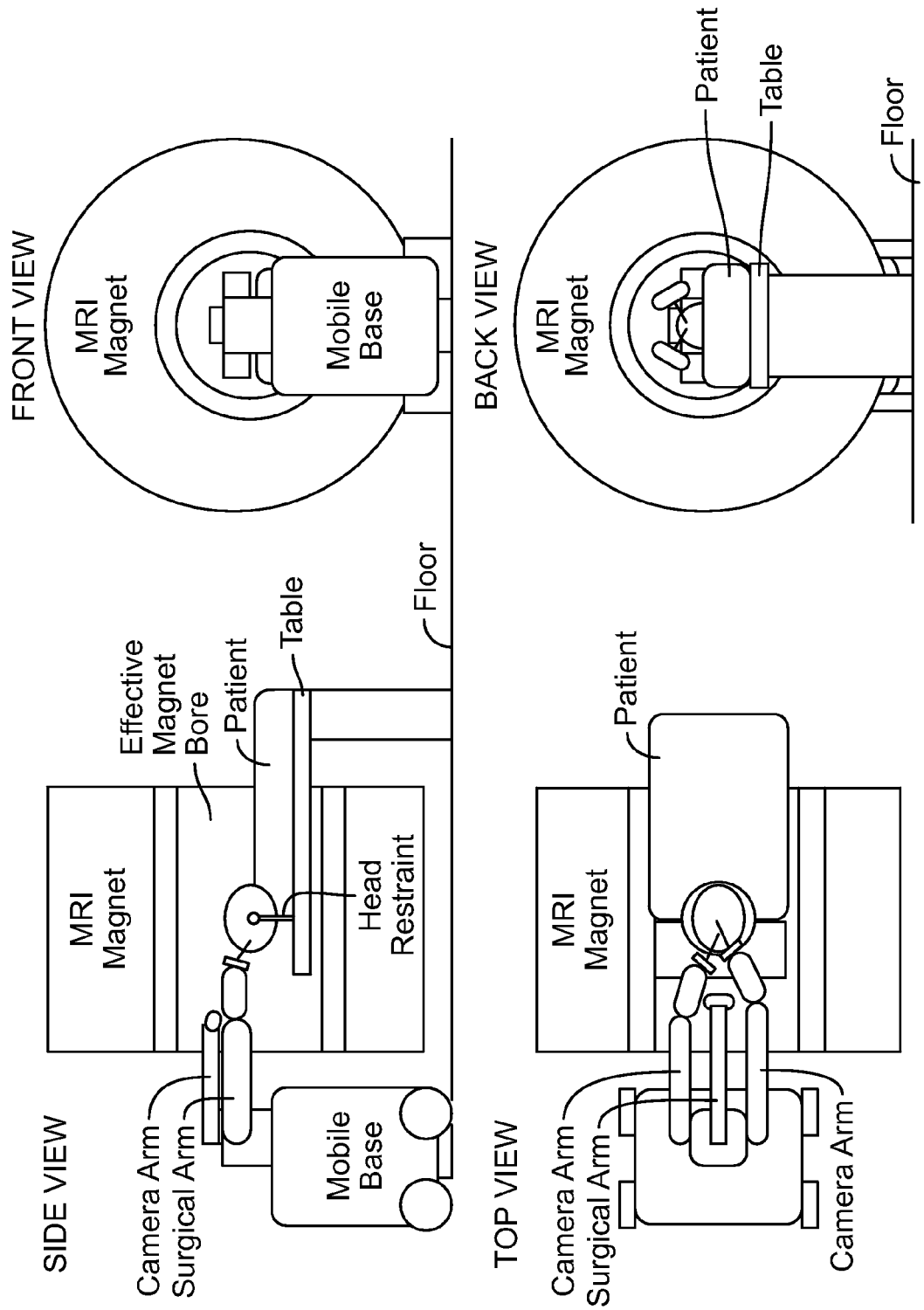
FIG. 10A shows schematic side, top, front and back views of the robot used with an open bore MRI magnet.

The robot therefore can be used in the two arm arrangement for microsurgery in an unrestricted area outside of the closed bore magnet or for microsurgery within an open bore of a magnet should the arrangement of the magnet be suitable to provide the field of operation necessary for the two arms to operate. The two arms therefore can be used with separate tools to affect surgical procedures as described above. Such an arrangement in shown in FIG. 10A.

Within the bore of a closed magnet, there is insufficient room to receive both arms of the device so that the single arm can be used to effect stereotactic procedures. Such procedures include the insertion of a probe or cannula into a required location within the brain of the patient using the real time magnetic resonance images to direct the location and direction of the tool. Thus the single arm system can be used to carry out whatever procedures are possible with the single arm but procedures requiring two arms must be carried out by removing the patient from the closed bore moving the patient to a required location where sufficient field of operation is available, restoring the robot to its two arm configuration with the table top 112 removed and locating the robot at the required position relative to the patient and the operating table.

Figure 10B:
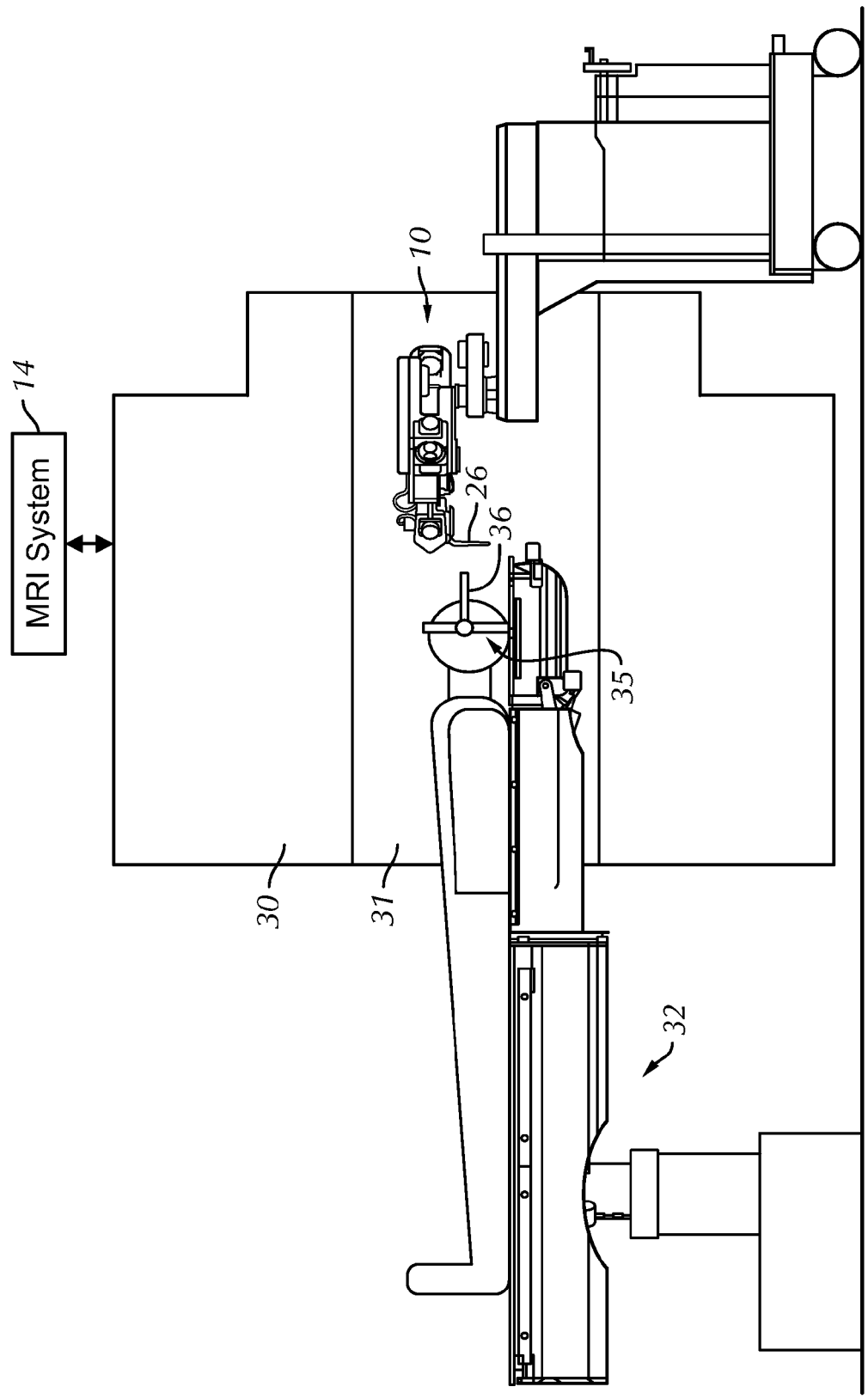
FIG. 10B is side elevational view of the robot in the configuration of FIG. 8 in conjunction with a patient table and the MRI magnet.

In FIG. 10B, the system is shown schematically in operation within the bore of a magnet 30 of the MRI system 14. The bore 31 is relatively small allowing a commercially available patient table 32 to carry the required portion of the patient into the bore to the required location within the bore. The field camera is used within the bore for observing the operation of the robot 10 and particularly the tool 26.

The registration system 15 (see FIG. 11) includes a mount 35 fixed to the head of the patient and including fiducial markers 36 carried on the mount. The mount is of a conventional head clamp construction commercially available. The fiducial markers are small objects which are located at fixed positions around the head of the patient in a predetermined configuration or array which can be located by the registration system so as to properly orient the registration system relative to the image generated by the MRI system 14. Thus the fiducial markers are formed of a material which is visible on the MR image so that the markers can be seen in the image as displayed on the monitor 16.

The same fiducial markers can be used in the MRI system even when the robot is not used in the MRI system for carrying out any procedures so that the image generated on the MRI system is registered relative to the fiducial markers or points located on the head of the patient.

Figure 11:
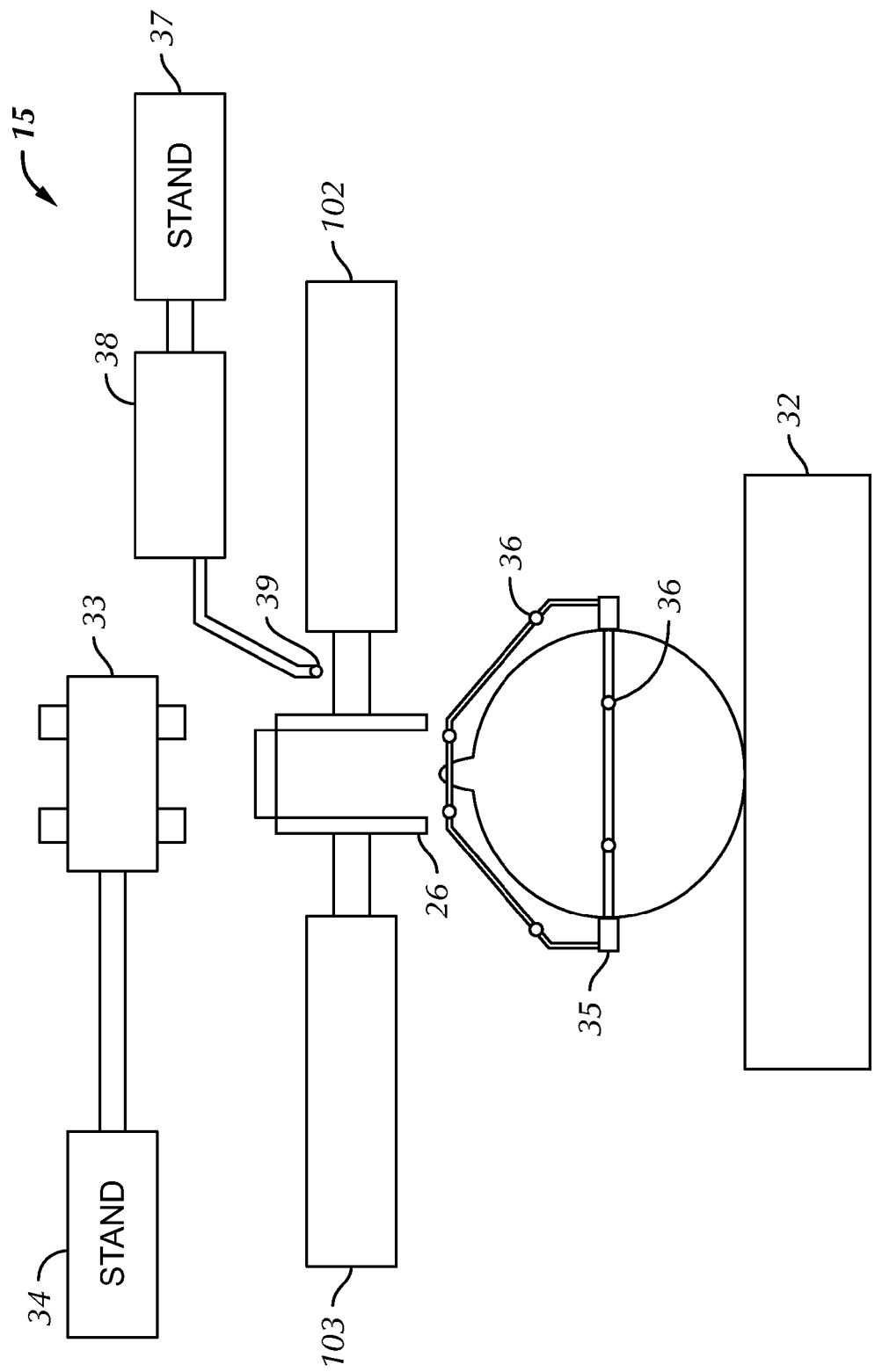
FIG. 11 is an end elevational view of a patient operating table and including the robot in co-operation with the microscope and location registration system.

As shown in FIG. 11, the patient on the table 32 is moved to the operating position which is accessible by the arms 102 and 103 and the tools 26 carried thereby. The patient carries the head restraint 35 which is fixed in the same position relative to the head of the patient as it was during the MRI process including the fiducial markers 36.

At the operating position on the table 32 is located the microscope 33 on the stand 34 which is moved to position the microscope to view the operating site at the operating location on the table 32.

The registration system 15 includes a stand 37 carrying a registration probe and associated control system 38 with the probe including a probe tip 39. The registration system 38 is mounted at a fixed position so that the location of the probe tip 39 in X, Y and Z coordinates can be located and determined by the registration system for communication to the controller 12.

Thus, with the patient fixed in place by the clamp 35, the position of each of the fiducial markers 36 is identified by the tip 39 thus providing to the system the co-ordinates of that fiducial marker. In addition the instantaneous position of the tip of the tool 26 is input into the same system thus registering the tool tip relative to the fiducial markers and therefore relative to the image displayed on the monitor 16.

The system is therefore operated so that the controller 12 operates to move the tool tip to a required position and at the same time indicates to the display system the actual location of the tool tip in the registered space defined by the fiducial markers and displayed on the monitor 16. The surgeon is therefore able to view the location of the tool tip on the monitor 16 relative to the previously obtained image and maintain the registration of those images.

In procedures carried out during the MR imaging process, the tool tip can be formed in manner which allows it to be visible in the image so that the surgeon obtains a real time image from the MRI system which locates the tool tip relative to the volume of interest visible on the monitor displaying the image.

The end effector is shown in FIGS. 12 through 17. The tool 26 is mounted on its upper end in the role actuator 148 so as to extend downwardly therefrom to the tip 40. The upper end of the tool is supported while allowing some side to side and front to back movement of the tool relative to the actuator 148. This movement is constrained by a collar at the actuator 149 which surrounds the tool and holds the tool along the axis of the actuator 148.

The tool support mechanism 148 allows rotation about the longitudinal axis 42 of the tool by a drive gear 150 actuated by a further motor P. Thus the tool, while held on the axis 42 can be rotated around its length to move the tip 40 of the tool around the axis.

Actuation of the tool is effected by moving the actuator 149 longitudinally of the axis 42. For this purpose the actuator 149 is mounted on a slide 43 carried in a track 44 and driven by a suitable mechanism along the track 44 so as to accurately locate the position of the actuator 149 along the length of the tool.

Figure 12:
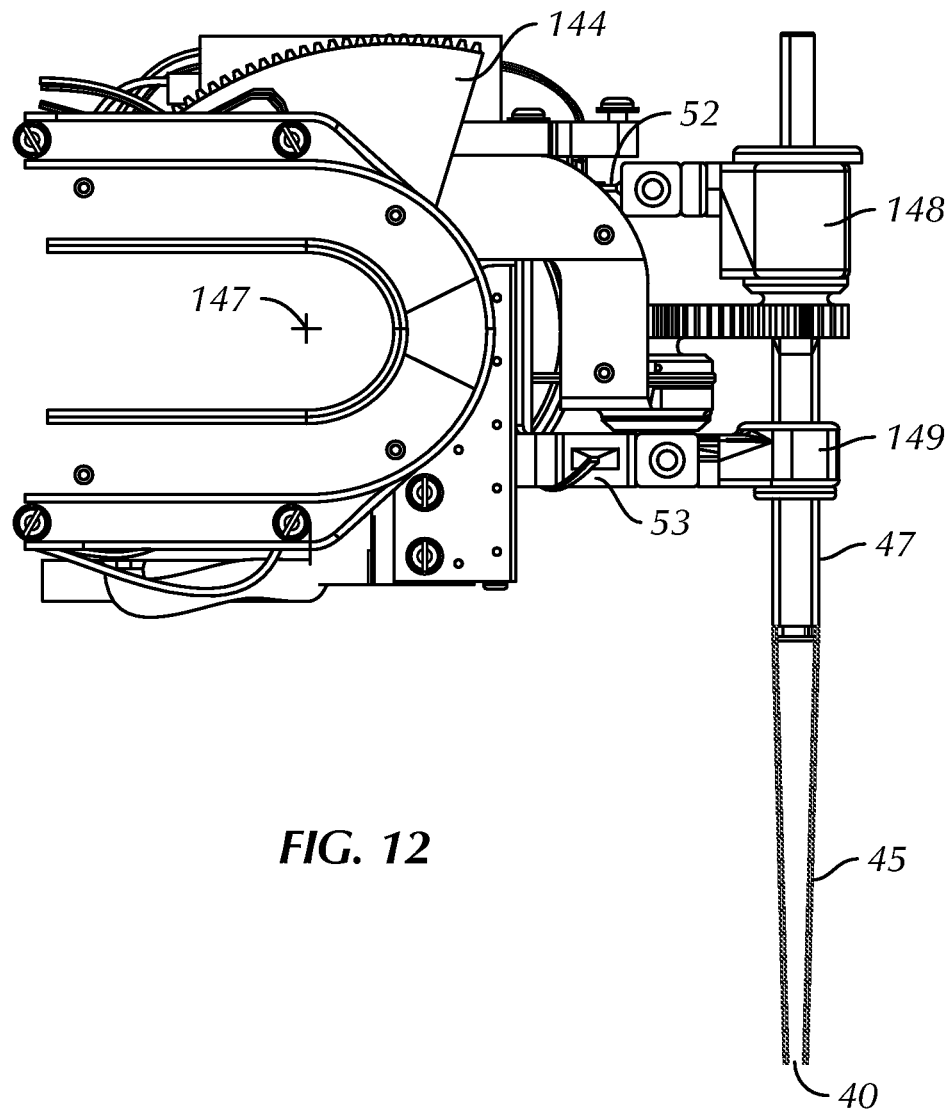
FIG. 12 is an enlarged side elevational view of the end effector including a pair of forceps mounted in the end effector.
Figure 13:
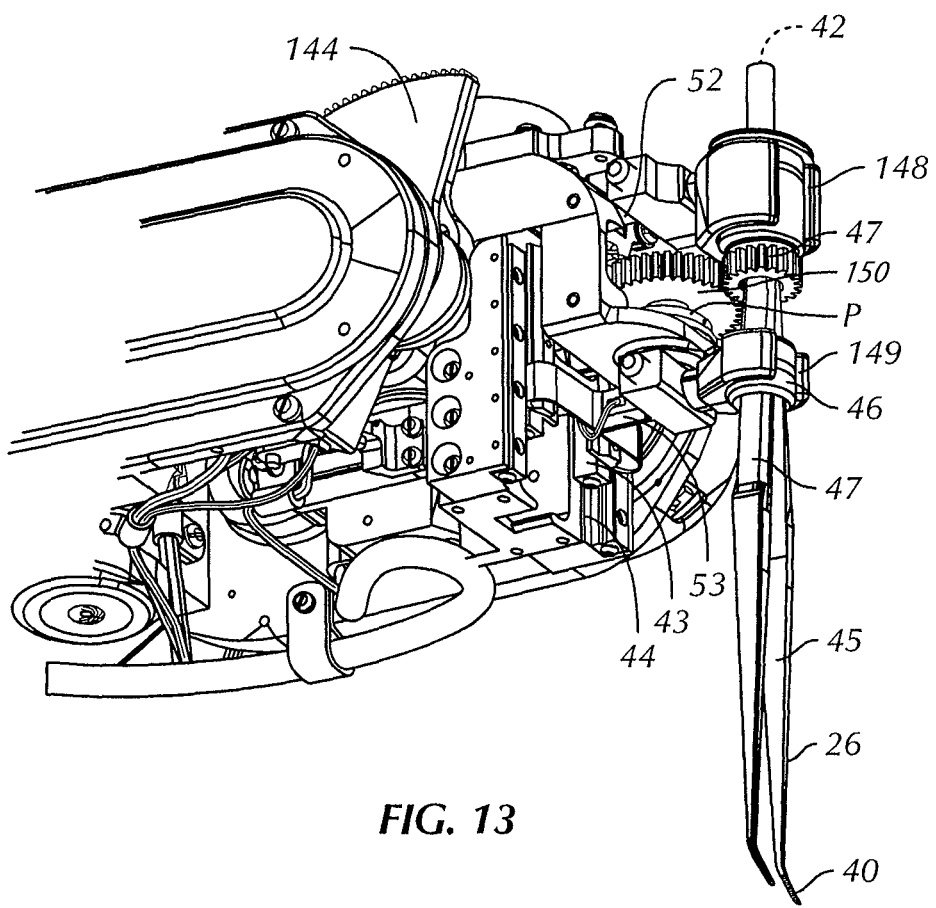
FIG. 13 is an enlarged isometric view of the end effector of FIG. 12.

In the example shown in FIGS. 12 and 13, the tool comprises forceps 45 which are actuated by moving the ring 46 of the actuator 149 along ramp surfaces 47 on the sides of the blades of the forceps 45. Thus the position axially of the ring 46 along the ramp surfaces 47 determines the spacing of the tips of the forceps.

Detection of the forces is applied on the tip 40 by an object engaged by the tip 40 is effected by top and bottom flexure detection components 52 and 53. Thus the actuator 148 is mounted on the top flexure component which is arranged to detect forces along the axis 42. The bottom flexure component is attached to the actuator 149 and is used to detect side to side and front to back forces in the X, Y plane.

Suitable flexure detection components are commercially available and different types can be used. For use in the magnet, however, the detection components must be MRI compatible.

One suitable example of a flexure detection system is that which uses a known optical detection system. Thus the flexure component includes a member which is flexed in response to the forces and the flexure of which changes the characteristics of reflected light within the member. Fiber optic cables supply a light source and receive the light component from the reflection, communicating the reflected light through the arm to a control module within the cabinet of the robot. Thus forces flexing the member in response to engagement of the tip of the tool with an object are communicated to the control module within the cabinet which converts the reflected light to an electrical signal proportional to the forces applied.

The control module in the cabinet communicates the electrical signals proportional to the forces to the controller 12 of the system. These forces are then amplified using conventional amplification systems and applied to the hand controllers so as to provide the previously described haptic effect to the surgeon at the hand controllers.

Figure 14:
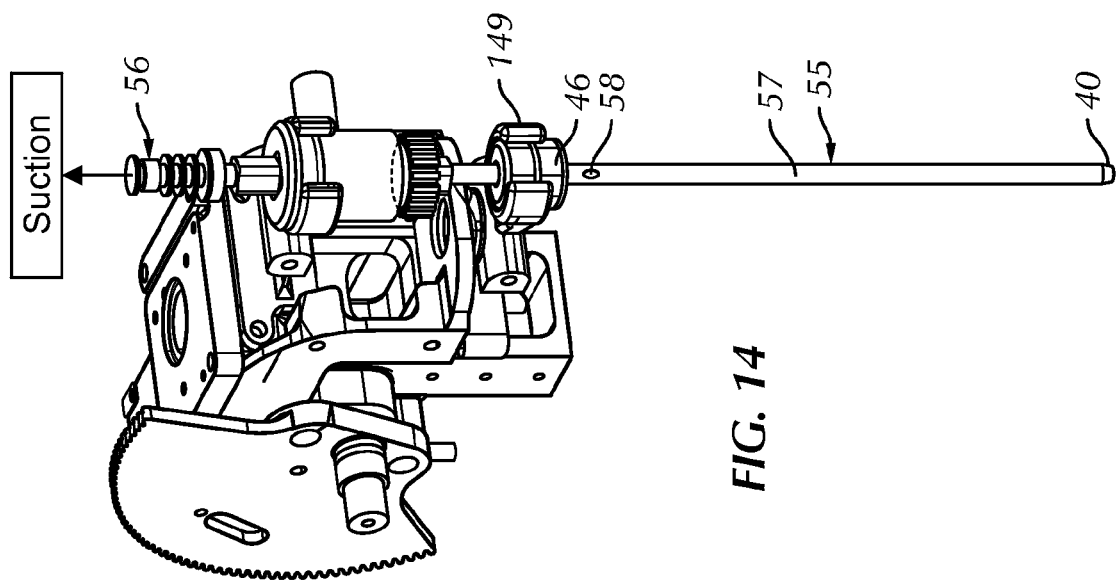
Figure 17:
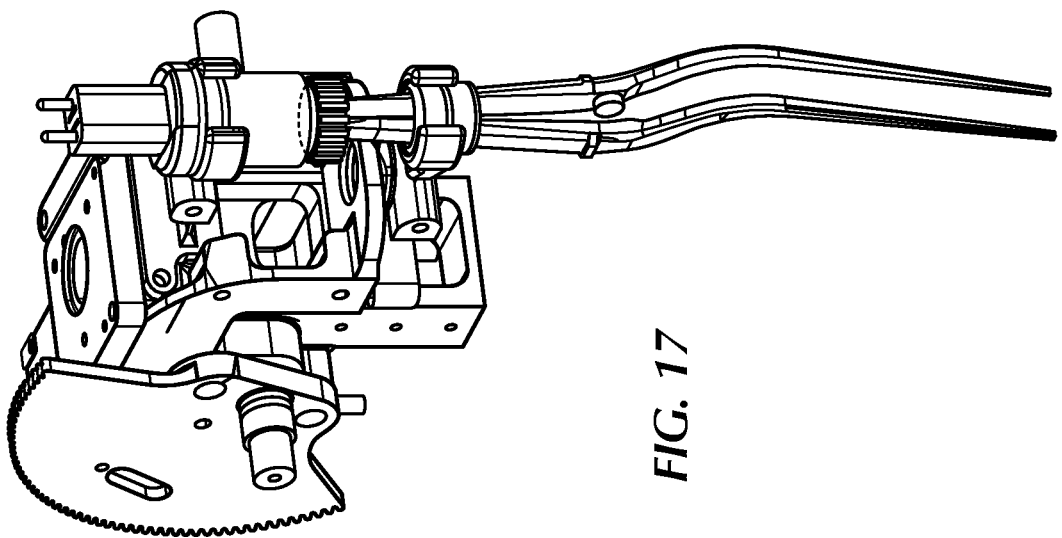

In FIG. 14 is shown a suction tool 55 which is used in replacement for the forceps shown in FIG. 13. Thus the forceps are removed by sliding the tool 26 longitudinally out of its engagement with the upper roll actuator 148. Thus the tool is removed from the ring 46 of the lower actuator 149. The suction tool 55 includes a connection 56 to a source of suction for applying a suction effect at the tip 40 of the suction tool. The amount of suction applied at the tip 40 relative to the suction source is controlled by moving the actuator ring 46 longitudinally of the tube 57 forming the tool. The tube 57 includes an inlet opening at the ring 46 which is partially or wholly covered by the ring 46. Thus when the opening 58 is fully exposed as shown in FIG. 14, the suction effect is minimized or removed so that little or no suction is applied at the tip 40. Partial covering of the hole 58 increases the suction effect up to a maximum when the hole is fully covered by the ring 46.

Figure 15:
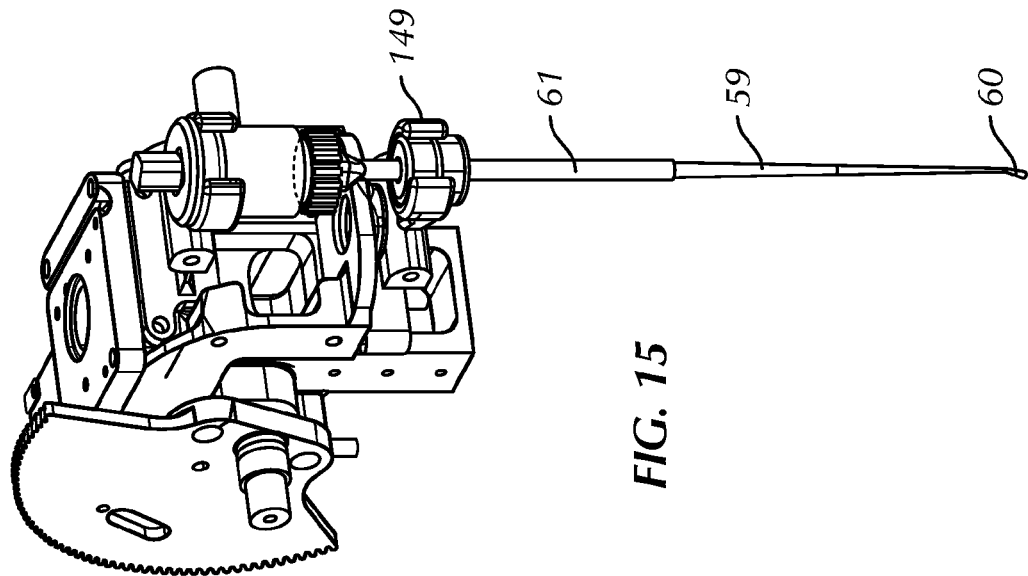
FIGS. 14, 15, 16 and 17 are isometric views of the main components of the end effector of FIG. 12 including four different tools, specifically a suction tool, a micro-dissection tool, micro-scissors and bipolar forceps respectively.

In FIG. 15 is shown a micro dissection tool 61 which is mounted as previously described. This tool simply comprises an elongated tool bar 59 with a tip 60 shaped for various well known functions which are available to the micro surgeon. As previously described, the tip can be rotated to a required orientation around the axis of the tool bar. In this tool, the lower actuator 149 is not operated but is merely used to detect side to side and front to rear forces as previously described.

Figure 16:
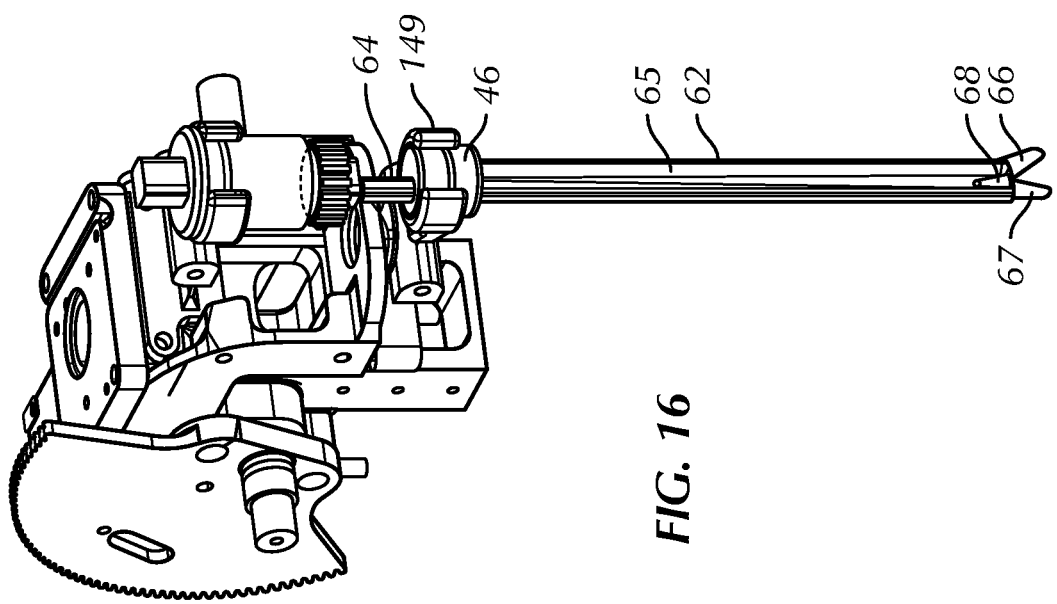

In FIG. 16 is shown a micro scissors tool 62 which is mounted in the upper and lower actuators as previously described. The scissors include a tool bar which is held at its upper end 64 by the upper actuator, together with an actuator rod 65 which is carried by the lower actuator 149. Upward and downward movement of the rod 65 actuates one blade 66 of a pair of scissors blades 66 and 67 in a cutting action by pivoting the blade 66 about a suitable support pivot 68.

The invention claimed is:

1. A surgical robotic system end effector configured to hold a surgical tool, the end effector comprising:
   a first actuator configured to roll the surgical tool about a longitudinal axis when held by the end effector and comprising a first flexure detection component for detecting force on the surgical tool along the longitudinal axis, wherein the first flexure detection component comprises optical strain sensors;
   a collar configured to surround a portion of the surgical tool; and
   a second actuator operable to move the collar relative to the surgical tool along the longitudinal axis and comprising a second flexure detection component for detecting force on the surgical tool in at least two different directions that are perpendicular to the direction of the longitudinal axis, wherein the second flexure detection component comprises optical strain sensors;
   wherein the end effector is for attachment to a robotic arm and actuatable in response to signals from the robotic arm.

2. The surgical robotic system end effector of claim 1, where the first actuator is configured to roll the surgical tool about the longitudinal axis using a driving gear.

3. The surgical robotic system end effector of claim 1, where the second actuator is mounted on a slide carried in a track.

4. A surgical robotic system comprising:
   an end effector for attachment to a robotic arm and actuatable in response to signals from the robotic arm, the end effector comprising:
   a tool support mechanism configured to hold a surgical tool defining a longitudinal axis;
   an actuator configured to move relative to the tool support mechanism along the longitudinal axis;
   a collar coupled to the actuator, and
   a flexure detection system configured to detect forces in X, Y, and Z directions on a surgical tool held by the end effector comprising:
     a first flexure detection component operatively associated with the tool support mechanism and arranged to detect force in the Z direction, wherein the first flexure detection component comprises optical strain sensors; and
     a second flexure detection component operatively associated with the actuator and arranged to detect force in the X and Y directions, wherein the second flexure detection component comprises optical strain sensors.

5. The surgical robotic system of claim 4, where the actuator is mounted on a slide, and the slide is carried in a track.

6. The surgical robotic system of claim 4, where the collar is configured to surround a portion of the surgical tool.

7. The surgical robotic system of claim 6, where the collar is configured to move along the longitudinal axis of the surgical tool to actuate the surgical tool.

8. The surgical robotic system of claim 4, the end effector further comprising a gear that rotates the surgical tool around the longitudinal axis of the surgical tool.

9. The surgical robotic system of claim 4, where the surgical tool is a pair of forceps.

10. The surgical robotic system of claim 9, where the pair of forceps comprises tips and ramp surfaces, and movement of the collar along the ramp surfaces determines the spacing of the tips.

11. The surgical robotic system of claim 4, where the surgical tool is a suction tool.

12. The surgical robotic system of claim 11, where the suction tool comprises an opening and the collar is configured to partially or wholly cover the opening depending on the location of the collar.

13. The surgical robotic system of claim 4, where the surgical tool is a micro scissors tool.

14. The surgical robotic system of claim 4, where the flexure detection system comprises one or more members configured to flex in response to force.

15. The surgical robotic system end effector of claim 1, where at least one flexure detection component comprises one or more members configured to flex in response to force.

16. A surgical robot end effector comprising:
a tool support mechanism configured to hold a surgical tool defining a longitudinal axis;
a first actuator configured to roll the surgical tool about the longitudinal axis;
a collar configured to surround a portion of the surgical tool and movable along the longitudinal axis of the surgical tool to transfer the surgical tool from an unactuated position to an actuated position, wherein the collar is longitudinally spaced apart from the tool support mechanism when the surgical tool is in the actuated position,
a second actuator operable to move the collar along the longitudinal axis of the surgical tool, and
a flexure detection system comprising:
a first flexure detection component operatively associated with the tool support mechanism and arranged to detect force in the Z direction, wherein the first flexure detection component comprises optical strain sensors; and
a second flexure detection component operatively associated with the second actuator and arranged to detect force in the X and Y directions, wherein the second flexure detection component comprises optical strain sensors;
wherein the end effector is for attachment to a robotic arm and actuatable in response to signals from the robotic arm.

\* \* \* \* \*